US 9,512,452 B2

(12) United States Patent
Kino et al.

(10) Patent No.: US 9,512,452 B2
(45) Date of Patent: Dec. 6, 2016

(54) L-LYSINE HYDROXYLASE AND PRODUCTION METHOD FOR HYDROXY-L-LYSINE AND HYDROXY-L-PIPECOLIC ACID USING SAME

(71) Applicant: API Corporation, Tokyo (JP)

(72) Inventors: Kuniki Kino, Tokyo (JP); Ryotaro Hara, Tokyo (JP); Ryoma Miyake, Kanagawa (JP); Hiroshi Kawabata, Kanagawa (JP)

(73) Assignee: API Corporation, Tokyo (JP)

( * ) Notice: Subject to any disclaimer, the term of this patent is extended or adjusted under 35 U.S.C. 154(b) by 0 days.

(21) Appl. No.: 14/431,193

(22) PCT Filed: Feb. 18, 2014

(86) PCT No.: PCT/JP2014/053774
§ 371 (c)(1),
(2) Date: Mar. 25, 2015

(87) PCT Pub. No.: WO2014/129459
PCT Pub. Date: Aug. 28, 2014

(65) Prior Publication Data

US 2015/0259715 A1    Sep. 17, 2015

(30) Foreign Application Priority Data

Feb. 19, 2013    (JP) .................................. 2013-030311

(51) Int. Cl.
| C12P 13/04 | (2006.01) |
| C12P 13/08 | (2006.01) |
| C12P 17/12 | (2006.01) |
| C12N 9/02 | (2006.01) |

(52) U.S. Cl.
CPC ............ *C12P 13/08* (2013.01); *C12N 9/0071* (2013.01); *C12P 13/04* (2013.01); *C12P 17/12* (2013.01); *C12Y 114/11004* (2013.01); *C12Y 114/11* (2013.01); *Y02P 20/52* (2015.11)

(58) Field of Classification Search
None
See application file for complete search history.

(56) References Cited

U.S. PATENT DOCUMENTS

| 7,425,530 | B2 | 9/2008 | Thibaut et al. |
| 2003/0199541 | A1 | 10/2003 | Lampilas et al. |

FOREIGN PATENT DOCUMENTS

| EP | 2876156 A1 | 5/2015 |
| EP | 2889288 A1 | 7/2015 |
| JP | 2004/505088 A | 2/2004 |
| JP | 2005-095167 | 4/2005 |
| JP | 2010-088395 | 4/2010 |
| WO | WO-02/101003 A2 | 12/2002 |
| WO | WO-2015098774 A1 | 7/2015 |

OTHER PUBLICATIONS

Sang, H., Mechanisms of Development 121:1179-1186, 2004.*
Tsung et al., J. Biol. Chem. 237:1194-1197, 1962.*
Supplementary Partial European Search Report from Application No. EP 14 75 4464 dated Oct. 20, 2015.
Database UniProt [Online] Nov. 28, 2012—Database accession No. A5FF23.
Extended European Search Report in EP Application No. 14754464.7 dated Feb. 9, 2016, 29 pages.
Database UniProt [Online] Jul. 11, 2012—Database accession No. G8T8D0.
Database UniProt [Online] Feb. 22, 2012—Database accession No. A4AK12.
Supplementary Partial European Search Report from Application No. EP 14 75 4464 dated Sep. 30, 2015.
Database UniProt [Online] Nov. 28, 2012—Database accession No. A55523.
Database UniProt [Online] Feb. 6, 2013—Database accession No. A6WF32.
Database UniProt [Online] Nov. 28, 2012—Database accession No. C7PLM6.
Database UniProt [Online] Dec. 14, 2011—Database accession No. D7W326.
International Preliminary Report on Patentability and Written Opinion in International Application No. PCT/JP2014/053774 dated Sep. 3, 2015, 8 pages.

(Continued)

*Primary Examiner* — David J Steadman
(74) *Attorney, Agent, or Firm* — Marshall, Gerstein & Borun LLP

(57) ABSTRACT

The present invention aims to provide a method for efficiently producing hydroxy-L-lysine. The present invention provides a method for producing hydroxy-L-lysine, the method comprising allowing 2-oxoglutarate-dependent L-lysine hydroxylase, a cell containing 2-oxoglutarate-dependent L-lysine hydroxylase, a processed product of the cell, and/or a culture broth obtained by culturing the cell, to act on L-lysine to produce hydroxy-L-lysine represented by the following General Formula (I) (wherein each of $R^1$, $R^2$ and $R^3$ represents a hydrogen atom or hydroxyl group, with the proviso that at least one of $R^1$, $R^2$ and $R^3$ represents a hydroxyl group).

9 Claims, 2 Drawing Sheets

(56) References Cited

OTHER PUBLICATIONS

Coulon et al., "An Efficient Synthesis of (2S,3R)-3-Hydroxylysine via Ruthenium Catalyzed Asymmetric Hydrogenation", Tetrahedron Letters 39 (1998), pp. 6467-6470.
Kinder Jr., et al., "Total Syntheses of Bengamides B and E", J. Org. Chem, 66, 2001, pp. 2118-2122.
Yasuda et al., "Enzymatic Synthesis of Cyclic Amino Acids by N-methyl-L-amino Acid Dehydrogenase from Pseudomonas Putida", Tetrahedron: Asymmetry 17, 2006, pp. 1775-1779.
Tsotsou et al., "Biochemical Characterisation of Recombinant Streptomyces Pristinaespiralis L-lysine Cyclodeaminase", Biochimie 89, 2007, pp. 591-604.
Gillard et al., "Preparation of (2S,4R)-4-Hydroxypipecolic Acid and Derivatives", J. Org. Chem., 61, 1996, pp. 2226-2231.
Shibasaki et al., "Microbial Proline 4-Hydroxylase Screening and Gene Cloning", Applied and Environmental Microbiology, vol. 65, No. 9, Sep. 1999, pp. 4028-4031.
Hibi et al., "Characterization of Bacillus Thuringiensis L-Isoleucine Dioxygenase for Production of Useful Amino Acids", Applied and Environmental Microbiology, vol. 77, No. 19, Oct. 2011, pp. 6926-6930.
Search Report in International Application No. PCT/JP2014/053774 dated May 20, 2014.
Accession No. A5FF23 dated Jun. 12, 2007.
Accession No. A6WF32 dated Aug. 21, 2007.
Accession No. C7PLM6 dated Oct. 13, 2009.
Accession No. D7W326 dated Oct. 5, 2010.
Accession No. G8T8D0 dated Feb. 22, 2012.
Accession No. A4AK12 dated Apr. 3, 2007.
Puistola et al., "Studies on the Lysyl Hydroxylase Reaction", Biochimica et Biophysica Acta, 611, 1980, pp. 40-50.

* cited by examiner

| Enzyme | Peak area | |
|---|---|---|
| | 3-HYL | L-Lys |
| Hyl-2 (ABS05421) | 1100999 | 909238 |
| Hyl-6 (EAR24255) | 551782 | 1170588 |

L-LYSINE HYDROXYLASE AND PRODUCTION METHOD FOR HYDROXY-L-LYSINE AND HYDROXY-L-PIPECOLIC ACID USING SAME

TECHNICAL FIELD

The present invention relates to a method for producing hydroxy-L-lysine using a novel lysine hydroxylase, and a method for producing hydroxy-L-pipecolic acid using the resulting hydroxy-L-lysine.

BACKGROUND ART

Hydroxy-L-lysine is an intermediate useful as an intermediate for pharmaceuticals and the like. For example, it is known that (3R)-hydroxy-L-lysine can be used as a precursor of a protein kinase C inhibitor (−)-balanol (Non-patent Document 1), and that (5R)-hydroxy-L-lysine can be used as a precursor of Bengamide B, which has antitumor activity (Non-patent Document 2). Hydroxy-L-lysine is reported to be useful as a material of hydroxy-L-pipecolic acid (Non-patent Documents 3 and 4). For example, (4R)-hydroxy-L-pipecolic acid can be used as a precursor of an HIV protease inhibitor palinavir (Non-patent Document 5), and (5S)-hydroxy-L-pipecolic acid and (5R)-hydroxy-L-pipecolic acid can be used as precursors of antimicrobial agents (Patent Document 1).

Examples of reported methods for synthesizing hydroxy-L-lysine include a method for synthesizing (3R)-hydroxy-L-lysine by asymmetric hydrogenation using a Ru catalyst (Non-patent Document 1).

Amino acid hydroxylases are useful enzymes for production of intermediates for pharmaceuticals and the like, and proline 4-hydroxylase (Non-patent Document 6) and L-isoleucine dioxygenase (Non-patent Document 7) have been reported before. However, enzymes that act on L-lysine have not yet been reported.

PRIOR ART DOCUMENTS

Patent Document

Patent Document 1: Japanese Translated PCT Patent Application Laid-open No. 2004-505088

Non-Patent Documents

Non-patent Document 1: Coulon et al., Tetrahedron Lett., 1998, 39, 6467
Non-patent Document 2: Kinder et al., J. Org. Chem., 2001, 66, 2118
Non-patent Document 3: Yasuda et al., Tetrahedron Asymm., 2006, 17, 1775
Non-patent Document 4: Tsotsou et al., Biochemie, 2007, 89, 591
Non-patent Document 5: Gillard et al., J. Org. Chem., 1996, 61, 2226
Non-patent Document 6: Shibasaki et al., Appl. Environ. Microbiol., 1999, 65, 4028
Non-patent Document 7: Hibi et al., Appl. Environ. Microbiol., 2011, 77, 6926

SUMMARY OF THE INVENTION

Problems to be Solved by the Invention

In the synthesis method for hydroxy-L-lysine described in Non-patent Document 1, preparation of the material is laborious, and the cost of preparation and recycling of the catalyst is high. Therefore, a more efficient synthesis method has been demanded.

An object of the present invention is to provide a novel, inexpensive, and simple method for production of hydroxy-L-lysine having higher optical purity.

Means for Solving the Problems

In order to solve the above problems, the present inventors intensively studied on a method for producing optically active hydroxy-L-lysine. As a result, the inventors discovered that homologue proteins of L-arginine-β hydroxylase VioC, whose isolation as proteins has not been reported so far and whose functions have been unknown, have 2-oxoglutarate-dependent L-lysine hydroxylase activity. The inventors also discovered that, by preparing a transformant using DNA encoding each protein and allowing the transformed cell, a processed product thereof, and/or a culture broth thereof to act on L-lysine, highly optically pure hydroxy-L-lysine can be obtained at high concentration. In addition, the inventors discovered that hydroxy-L-pipecolic acid can be produced using the resulting hydroxy-L-lysine. The present invention was achieved based on these discoveries.

That is, the present invention can be summarized as follows.

(1) A method for producing hydroxy-L-lysine, the method comprising allowing 2-oxoglutarate-dependent L-lysine hydroxylase, a cell containing 2-oxoglutarate-dependent L-lysine hydroxylase, a processed product of the cell, and/or a culture broth obtained by culturing the cell, to act on L-lysine to produce hydroxy-L-lysine represented by the following General Formula (I):

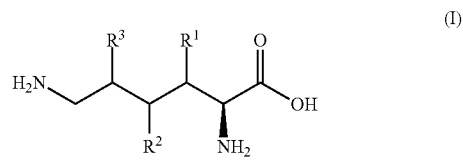

(wherein each of $R^1$, $R^2$ and $R^3$ represents a hydrogen atom or hydroxyl group, with the proviso that at least one of $R^1$, $R^2$ and $R^3$ represents a hydroxyl group).

(2) The method for producing hydroxy-L-lysine according to (1), wherein the 2-oxoglutarate-dependent L-lysine hydroxylase comprises the polypeptide shown in the following (A), (B), or (C):

(A) a polypeptide comprising the amino acid sequence of SEQ ID NO:2, 4, 6, 8, 10, or 12;

(B) a polypeptide comprising the amino acid sequence of SEQ ID NO:2, 4, 6, 8, 10, or 12 except that one or several amino acids are deleted, substituted, and/or added, which polypeptide has 2-oxoglutarate-dependent L-lysine hydroxylase activity; or (C) a polypeptide comprising an amino acid sequence with an identity of not less than 60% to the amino acid sequence of SEQ ID NO:2, 4, 6, 8, 10, or 12, which polypeptide has 2-oxoglutarate-dependent L-lysine hydroxylase activity.

(3) The method for producing hydroxy-L-lysine according to (1) or (2), wherein the cell comprising 2-oxoglutarate-dependent L-lysine hydroxylase is a cell transformed with a DNA encoding the 2-oxoglutarate-dependent L-lysine hydroxylase.

(4) The method for producing hydroxy-L-lysine according to (3), wherein the DNA encoding 2-oxoglutarate-dependent L-lysine hydroxylase comprises the DNA of the following (D), (E), or (F):
  (D) DNA comprising the nucleotide sequence of SEQ ID NO:1, 3, 5, 7, 9, or 11;
  (E) DNA comprising the nucleotide sequence of SEQ ID NO:1, 3, 5, 7, 9, or 11 except that one or several nucleotides are substituted, deleted, and/or added, which DNA encodes a polypeptide having 2-oxoglutarate-dependent L-lysine hydroxylase activity; or
  (F) DNA comprising a nucleotide sequence which hybridizes with the complementary strand of the nucleotide sequence of SEQ ID NO:1, 3, 5, 7, 9, or 11 under stringent conditions, which DNA encodes a polypeptide having 2-oxoglutarate-dependent L-lysine hydroxylase activity.

(5) The method for producing hydroxy-L-lysine according to any one of (1) to (4), wherein the 2-oxoglutarate-dependent L-lysine hydroxylase, cell containing the 2-oxoglutarate-dependent L-lysine hydroxylase, processed product of the cell, and/or culture broth obtained by culturing the cell, is/are allowed to act on the L-lysine in the presence of 2-oxoglutaric acid and ferrous ion.

(6) A method for producing hydroxy-L-pipecolic acid, the method comprising:
  producing hydroxy-L-lysine by the production method according to any one of (1) to (5);
  allowing the resulting hydroxy-L-lysine to react with at least one enzyme selected from the group consisting of L-amino acid oxidase, L-amino acid dehydrogenase, and L-amino acid transferase, or with amino acid racemase and at least one enzyme selected from the group consisting of D-amino acid oxidase, D-amino acid dehydrogenase, and D-amino acid transferase, to produce a compound represented by the following General Formula (II):

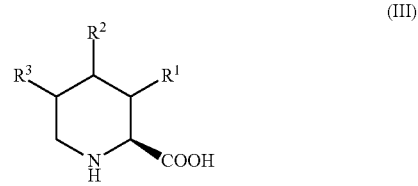

(wherein $R^1$, $R^2$, and $R^3$ have the same meanings as in General Formula (I)); and
  allowing N-methyl-L-amino acid dehydrogenase to act on the resulting compound to produce hydroxy-L-pipecolic acid represented by the following General Formula (III):

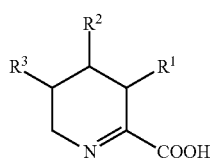

(wherein $R^1$, $R^2$, and $R^3$ have the same meanings as in General Formula (I)).

(7) A method for producing hydroxy-L-pipecolic acid, the method comprising:
  producing hydroxy-L-lysine by the production method according to any one of (1) to (5);
  allowing the resulting hydroxy-L-lysine to react with at least one enzyme selected from the group consisting of L-lysine 6-oxidase, L-lysine 6-dehydrogenase, and L-lysine 6-transferase, to produce a compound represented by the following General Formula (IV):

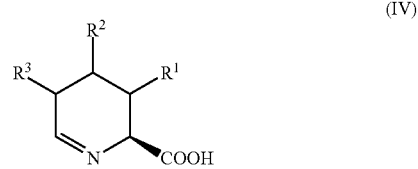

(wherein $R^1$, $R^2$, and $R^3$ have the same meanings as in General Formula (I)); and
  allowing pyrroline-5-carboxylate reductase to act on the resulting compound to produce hydroxy-L-pipecolic acid represented by the following General Formula (III):

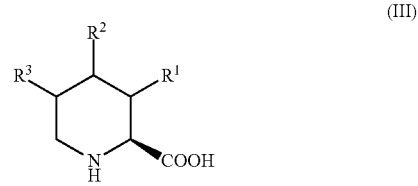

(wherein $R^1$, $R^2$, and $R^3$ have the same meanings as in General Formula (I)).

(8) A method for producing hydroxy-L-pipecolic acid, the method comprising:
  producing hydroxy-L-lysine by the production method according to any one of (1) to (5); and
  allowing lysine cyclodeaminase to act on the resulting hydroxy-L-lysine to produce hydroxy-L-pipecolic acid represented by the following General Formula (III):

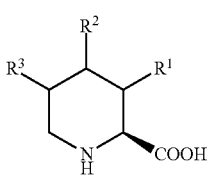

(wherein $R^1$, $R^2$, and $R^3$ have the same meanings as in General Formula (I)).

(9) A 2-oxoglutarate-dependent L-lysine hydroxylase protein having activity to act on L-lysine to produce hydroxy-L-lysine, and comprising the polypeptide of the following (A), (B), or (C):
  (A) a polypeptide comprising the amino acid sequence of SEQ ID NO:2, 4, 6, 8, 10, or 12;
  (B) a polypeptide comprising the amino acid sequence of SEQ ID NO:2, 4, 6, 8, 10, or 12 except that one or several amino acids are deleted, substituted, and/or added, which polypeptide has 2-oxoglutarate-dependent L-lysine hydroxylase activity; or
  (C) a polypeptide comprising an amino acid sequence with an identity of not less than 60% to the amino acid sequence of SEQ ID NO:2, 4, 6, 8, 10, or 12, which polypeptide has 2-oxoglutarate-dependent L-lysine hydroxylase activity.

Effect of the Invention

By the present invention, hydroxy-L-lysine can be efficiently produced, and highly optically pure hydroxy-L-lysine can be obtained. From the resulting hydroxy-L-lysine, highly optically pure hydroxy-L-pipecolic acid can be efficiently produced.

MODE FOR CARRYING OUT THE INVENTION

Figure 1:
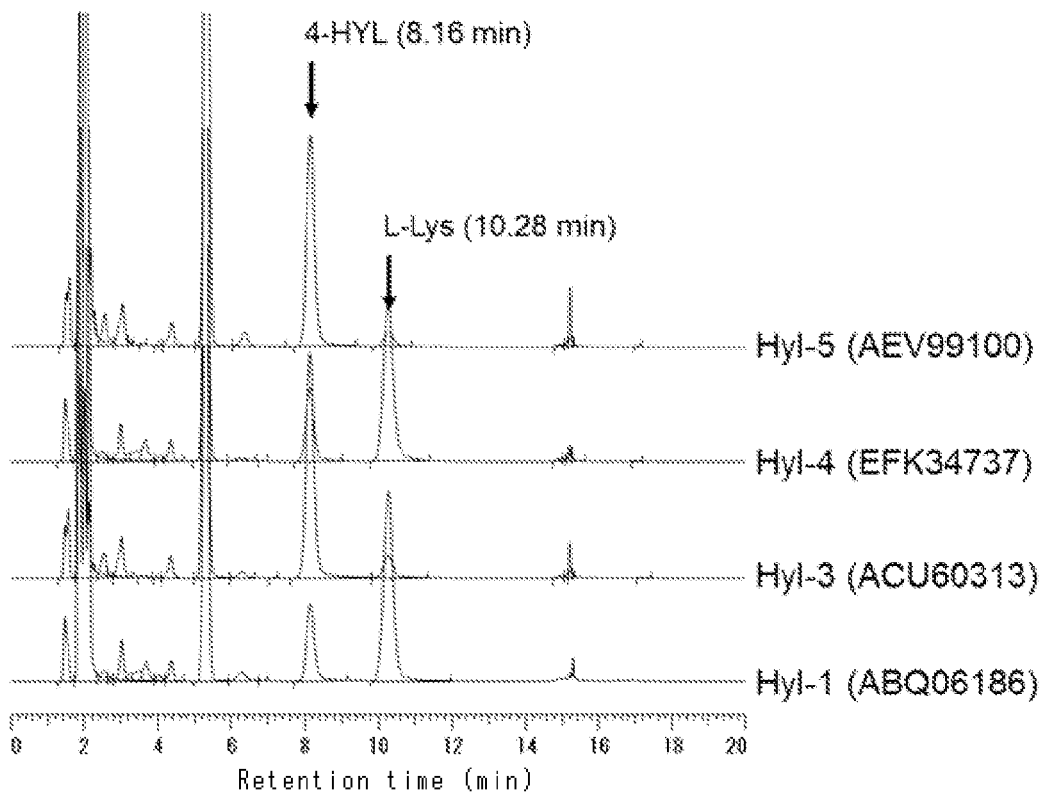
FIG. 1 is a diagram illustrating conversion of L-lysine to 4-hydroxylysine by Hyl-1, 3, 4, or 5.

The present invention is described below in detail.
<Method for Production of Hydroxy-L-Lysine Using 2-Oxoglutarate-Dependent L-Lysine Hydroxylase>

The method for producing hydroxy-L-lysine of the present invention comprises allowing 2-oxoglutarate-dependent L-lysine hydroxylase, a cell containing 2-oxoglutarate-dependent L-lysine hydroxylase, a processed product of the cell, and/or a culture broth obtained by culturing the cell, to act on L-lysine. As described later, the method of the present invention is preferably carried out in the presence of 2-oxoglutaric acid and ferrous ion.

Since the 2-oxoglutarate-dependent L-lysine hydroxylase used in the present invention (hereinafter also referred to as "L-lysine hydroxylase of the present invention") has high regioselectivity and stereoselectivity in hydroxylation of L-lysine, highly optically pure hydroxy-L-lysine can be efficiently obtained using it.

The L-lysine hydroxylase in the present invention is not limited as long as the L-lysine hydroxylase has 2-oxoglutarate-dependent L-lysine hydroxylase activity. Preferably, the L-lysine hydroxylase has the amino acid sequence of SEQ ID NO: 2, 4, 6, 8, 10, or 12, or is a homologue of the amino acid sequence having 2-oxoglutarate-dependent L-lysine hydroxylase activity. That is, the L-lysine hydroxylase of the present invention preferably comprises the polypeptide of the following (A), (B), or (C):

(A) a polypeptide comprising the amino acid sequence of SEQ ID NO:2, 4, 6, 8, 10, or 12;

(B) a polypeptide comprising the amino acid sequence of SEQ ID NO:2, 4, 6, 8, 10, or 12 except that one or several amino acids are deleted, substituted, and/or added, which polypeptide has 2-oxoglutarate-dependent L-lysine hydroxylase activity; or (C) a polypeptide comprising an amino acid sequence with an identity of not less an 60% to the amino acid sequence of SEQ ID NO:2, 4, 6, 8, 10, or 12, which polypeptide has 2-oxoglutarate-dependent L-lysine hydroxylase activity.

Examples of the homologue of 2-oxoglutarate-dependent L-lysine hydroxylase comprising the amino acid sequence of SEQ ID NO: 2, 4, 6, 8, 10, or 12 which can be used in the present invention include, as described above in (B), a polypeptide comprising the amino acid sequence of SEQ ID NO:2, 4, 6, 8, 10, or 12 except that one or several amino acids are deleted, substituted, and/or added as long as the polypeptide retains 2-oxoglutarate-dependent L-lysine hydroxylase activity. The term "one or several amino acids" herein means, for example, 1 to 100, preferably 1 to 50, more preferably 1 to 20, still more preferably 1 to 10, especially preferably 1 to 5, amino acids.

As described above in (C), the homologue may also be a protein with a sequence identity of at least not less than 60%, preferably not less than 80%, more preferably not less than 90%, still more preferably not less than 95% to the entire amino acid sequence of SEQ ID NO:2, 4, 6, 8, 10, or 12 as long as the protein has 2-oxoglutarate-dependent L-lysine hydroxylase activity.

In the present description, the 2-oxoglutarate-dependent L-lysine hydroxylase activity means activity that adds a hydroxyl group to the carbon atom(s) at the 3-position, 4-position, and/or 5-position of L-lysine in a 2-oxoglutarate-dependent manner. Such activity can be confirmed by allowing the protein of interest, a cell expressing the protein, and/or a processed product of the cell to act as an enzyme in a reaction system comprising L-lysine as a substrate and 2-oxoglutaric acid as a coenzyme, and then measuring production of hydroxy-L-lysine as described below in the Examples.

The amino acid sequences of 2, 4, 6, 8, 10, and 12 are based on the genomic information of *Flavobacterium johnsoniae* UW101 strain, *Kineococcus radiotolerans* SRS30216 strain, *Chitinophaga pinensis* DSM2588 strain, *Chryseobacterium gleum* ATCC35910 strain, *Niastella koreensis* GR20-10 strain, and marine actinobacterium PHSC20C1, respectively.

The amino acid sequences of 2, 4, 6, 8, 10, and 12 are identical to GenBank accession Nos. ABQ06186, ABS05421, ACU60313, EFK34737, AEV99100, and EAR24255, respectively, which are amino acid sequences translated from DNA sequences predicted to encode proteins. None of these amino acid sequences have been reported to actually exist based on, for example, isolation of the proteins, and their protein functions have been totally unknown.

Since the L-lysine hydroxylases of the present invention comprising the amino acid sequence of SEQ ID NO:2, 6, 8, or 10 hydroxylate the 4-position of L-lysine, (2S,4R) hydroxy L-lysine can be produced thereby. Among these sequences, SEQ ID NO:8 is preferred because of high yield.

Since the L-lysine hydroxylases of the present invention comprising the amino acid sequence of SEQ ID NO:4 or 12 hydroxylate the 3-position of L-lysine, (2S,3S) hydroxy L-lysine can be produced thereby. Among these sequences, SEQ ID NO:12 is preferred because of high yield.

In the production method of the present invention, a plurality of 2-oxoglutarate-dependent L-lysine hydroxylases may be used in combination.

A 2-oxoglutarate-dependent L-lysine hydroxylase which can be used in the present invention can be obtained by purification from *Flavobacterium johnsoniae, Kineococcus radiotolerans, Chitinophaga pinensis, Chryseobacterium gleum, Niastella koreensis*, or marine actinobacterium, and can also be obtained by cloning of DNA encoding 2-oxoglutarate-dependent L-lysine hydroxylase using a known method such as PCR or hybridization, followed by allowing expression of the enzyme in an appropriate host.

Examples of the DNA encoding 2-oxoglutarate-dependent L-lysine hydroxylase comprising the amino acid sequence of SEQ ID NO:2, 4, 6, 8, 10, or 12 include DNAs comprising the nucleotide sequence of SEQ ID NO:1, 3, 5, 7, 9, or 11, respectively, and the DNA encoding 2-oxoglutarate-dependent L-lysine hydroxylase may be a homologue of DNA comprising the nucleotide sequence of SEQ ID NO:1, 3, 5, 7, 9, or 11 as long as the homologue encodes a protein having 2-oxoglutarate-dependent L-lysine hydroxylase activity. That is, examples of the DNA encoding the L-lysine hydroxylase of the present invention include the nucleotide sequences shown in the following (D), (E), and (F).

(D) DNA comprising the nucleotide sequence of SEQ ID NO:1, 3, 5, 7, 9, or 11;

(E) DNA comprising the nucleotide sequence of SEQ ID NO:1, 3, 5, 7, 9, or 11 except that one or several nucleotides are substituted, deleted, and/or added, which DNA encodes a polypeptide having 2-oxoglutarate-dependent L-lysine hydroxylase activity; or (F) DNA comprising a nucleotide sequence which hybridizes with the complementary strand of the nucleotide sequence of SEQ ID NO:1, 3, 5, 7, 9, or 11 under stringent conditions, which DNA encodes a polypeptide having 2-oxoglutarate-dependent L-lysine hydroxylase activity.

As described in (E), examples of the homologue include homologues comprising the nucleotide sequence of SEQ ID NO:1, 3, 5, 7, 9, or 11 except that one or several nucleotides are substituted, deleted, and/or added. The term "one or several nucleotides" herein means, for example, 1 to 300, preferably 1 to 150, more preferably 1 to 60, still more preferably 1 to 30, especially preferably 1 to 15, nucleotides.

As described in (F), the DNA homologue may be a DNA which hybridizes with the complementary strand of the nucleotide sequence of SEQ ID NO:1, 3, 5, 7, 9, or 11 under stringent conditions as long as the DNA homologue encodes a protein having 2-oxoglutarate-dependent L-lysine hydroxylase activity. Examples of the "stringent conditions" herein include conditions under which washing is carried out with 0.1×SSC and 0.1% SDS at 60° C.

Those skilled in the art can obtain the DNA homologue described above by introducing, as appropriate, a substitution, deletion, insertion, and/or addition mutation(s) to the DNA of SEQ ID NO:1, 3, 5, 7, 9, or 11 by site-specific mutagenesis (Nucleic Acids Res. 10, pp. 6487 (1982), Methods in Enzymol. 100, pp. 448 (1983), Molecular Cloning, PCR A Practical Approach IRL Press pp. 200 (1991)) or the like.

It is also possible to obtain amino acid information of 2-oxoglutarate-dependent L-lysine hydroxylase activity or nucleotide sequence information of DNA encoding it, by carrying out homology search using the amino acid sequence of SEQ ID NO:2, 4, 6, 8, 10, or 12 or part thereof, or the nucleotide sequence of SEQ ID NO:1, 3, 5, 7, 9, or 11 or part thereof against a database such as DNA Databank of JAPAN (DDBJ).

In the method for producing hydroxy-L-lysine of the present invention, 2-oxoglutarate-dependent L-lysine hydroxylase may be directly used for the reaction, but it is preferred to use a cell containing 2-oxoglutarate-dependent L-lysine hydroxylase, a processed product thereof, and/or a culture broth obtained by culturing the cell.

The cell containing 2-oxoglutarate-dependent L-lysine hydroxylase may be a cell such as a microorganism which inherently has 2-oxoglutarate-dependent L-lysine hydroxylase, but it is preferred to use a cell such as a microorganism transformed with a gene encoding 2-oxoglutarate-dependent L-lysine hydroxylase. The cell may be either a dead cell or live cell, and, for example, a resting cell or the like may be preferably used.

Examples of the processed product of the cell containing 2-oxoglutarate-dependent L-lysine hydroxylase include: processed cell products such as products prepared by treatment with an organic solvent, for example, acetone, dimethylsulfoxide (DMSO), or toluene, products prepared by treatment with a surfactant, products prepared by lyophilization, and products prepared by physical or enzymatic disruption; products prepared by extracting an enzyme fraction from the cell as a crude product or purified product; and products prepared by immobilizing any of these products on a carrier such as polyacrylamide gel, carrageenan gel, or the like.

Examples of the culture broth obtained by culturing the cell containing 2-oxoglutarate-dependent L-lysine hydroxylase include a suspension of the cell in a liquid medium, and, in cases where the cell is a secretory expression cell, examples of the culture broth include the supernatant obtained by removing the cell by centrifugation or the like, and a concentrate of the supernatant.

By inserting the thus isolated DNA encoding 2-oxoglutarate-dependent L-lysine hydroxylase into a known expression vector such that expression of the enzyme is possible, a 2-oxoglutarate-dependent L-lysine hydroxylase expression vector can be provided. By transforming a host cell with this expression vector, a transformant in which the DNA encoding 2-oxoglutarate-dependent L-lysine hydroxylase is introduced can be obtained. The transformant can also be obtained by incorporating the DNA encoding 2-oxoglutarate-dependent L-lysine hydroxylase into the chromosomal DNA of a host by homologous recombination or the like such that expression of the enzyme is possible.

Specific examples of the method for preparing the transformant include a method in which the DNA encoding 2-oxoglutarate-dependent L-lysine hydroxylase is introduced into a plasmid vector, phage vector, or virus vector which can be stably present in a host cell such as a microorganism, and the constructed expression vector is then introduced into the host cell, or a method in which the DNA is directly introduced into the host genome, and the genetic information is then transcribed and translated. In this process, an appropriate promoter is preferably linked to 5'-upstream of the DNA, and, in addition, an appropriate terminator is more preferably linked to 3'-downstream of the DNA in the host. Such a promoter and terminator are not limited as long as the promoter and the terminator are known to function in the cell to be used as the host. For example, "Fundamental Microbiology 8: Genetic Engineering, KYORITSU SHUPPAN CO., LTD." describes details of vectors, promoters, and terminators that can be used in host microorganisms.

The host microorganism to be transformed for expression of 2-oxoglutarate-dependent L-lysine hydroxylase is not limited as long as the host itself does not adversely affect the reaction of L-lysine, and specific examples of the host microorganism include the following microorganisms:

bacteria belonging to the genera *Escherichia, Bacillus, Pseudomonas, Serratia, Brevibacterium, Corynebacterium, Streptococcus, Lactobacillus*, and the like whose host vector systems have been established;

actinomycetes belonging to the genera *Rhodococcus, Streptomyces*, and the like whose host vector systems have been established;

yeasts belonging to the genera *Saccharomyces, Kluyveromyces, Schizosaccharomyces, Zygosaccharomyces, Yarrowia, Trichosporon, Rhodosporidium, Hansenula, Pichia, Candida*, and the like whose host vector systems have been established; and molds belonging to the genera *Neurospora, Aspergillus, Cephalosporium, Trichoderma*, and the like whose host vector systems have been established.

The procedure for construction of the transformant, the method for construction of a recombinant vector suitable for the host, and the method for culturing the host can be carried out according to techniques commonly used in the fields of molecular biology, bioengineering, and genetic engineering (for example, methods described in Molecular Cloning).

The following are examples of preferred host microorganisms, and preferred examples of the method of transformation, vector, promoter, terminator, and the like for each microorganism. The present invention is not limited by these examples.

For the genus Escherichia, especially Escherichia coli, examples of the plasmid vector include pBR and pUC plasmids, and examples of the promoter include promoters derived from lac (β-galactosidase), trp (tryptophan operon), tac, trc (fusion of lac and trp), and λ phage PL and PR. Examples of the terminator include terminators derived from trpA, phages, and rrnB ribosomal RNA.

For the genus Bacillus, examples of the vector include pUB110 plasmids and pC194 plasmids. Integration into the chromosome is also possible. Examples of the promoter and the terminator include those of genes of enzymes such as alkaline protease, neutral protease, and α-amylase.

For the genus Pseudomonas, examples of the vector include common host vector systems established in Pseudomonas putida, Pseudomonas cepacia, and the like; and a wide-host-range vector (containing genes required for autonomous replication derived from RSF1010 and the like) pKT240, which is based on a plasmid involved in degradation of toluene compounds, TOL plasmid (Gene, 26, 273-82 (1983)).

For the genus Brevibacterium, especially Brevibacterium lactofermentum, examples of the vector include plasmid vectors such as pAJ43 (Gene 39, 281 (1985)). Examples of the promoter and the terminator include promoters and terminators used in E. coli.

For the genus Corynebacterium, especially Corynebacterium glutamicum, examples of the vector include plasmid vectors such as pCS11 (JP 57-183799 A) and pCB101 (Mol. Gen. Genet. 196, 175 (1984)).

For Saccharomyces, especially Saccharomyces cerevisiae, examples of the vector include YRp, YEp, YCp, and YIp plasmids. Examples of promoters and terminators which may be used include those of the genes of enzymes such as alcohol dehydrogenase, glyceraldehyde-3-phosphate dehydrogenase, acid phosphatase, β-galactosidase, phosphoglycerate kinase, and enolase.

For the genus Schizosaccharomyces, examples of the vector include the plasmid vector derived from Schizosaccharomyces pombe described in Mol. Cell. Biol. 6, 80 (1986). In particular, pAUR224 is commercially available from Takara Shuzo Co., Ltd., and can be easily used.

In terms of the genus Aspergillus, Aspergillus niger, Aspergillus oryzae and the like are the best-studied species among molds. Plasmids, and integration into the chromosome are applicable to these species, and promoters for extracellular protease and amylase can be used (Trends in Biotechnology 7, 283-287 (1989)).

Host vector systems other than the above-described systems have also been established for various microorganisms, and those systems may be used as appropriate.

Various host/vector systems have been established for plants and animals, in addition to microorganisms. In particular, systems for allowing expression of a large amount of foreign protein in an animal such as an insect (e.g., silkworm) (Nature 315, 592-594 (1985)), or in a plant such as rapeseed, maize, or potato; and systems based on cell-free protein synthesis systems such as E. coli cell-free extracts and wheat germs; have been established, and may be preferably used.

In the production method of the present invention, 2-oxoglutarate-dependent L-lysine hydroxylase, a cell containing the enzyme, a processed product of the cell, and/or a culture broth obtained by culturing the cell, is/are allowed to act on a reaction substrate L-lysine in the presence of 2-oxoglutaric acid, to produce hydroxy-L-lysine represented by the following General Formula (I):

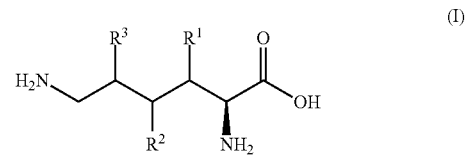

(wherein each of $R^1$, $R^2$ and $R^3$ represents a hydrogen atom or hydroxyl group, with the proviso that at least one of $R^1$, $R^2$ and $R^3$ represents a hydroxyl group).

$R^1$, $R^2$ and $R^3$ in the General Formula (I) may be selected in consideration of the compound which is to be finally obtained. In particular, one or two of $R^1$, $R^2$ and $R^3$ is/are preferably a hydroxyl group(s), and one of $R^1$, $R^2$ and $R^3$ is more preferably a hydroxyl group.

The production method of the present invention is not limited as long as 2-oxoglutaric acid; and 2-oxoglutarate-dependent L-lysine hydroxylase, a cell containing the enzyme, a processed product of the cell, and/or a culture broth obtained by culturing the cell; can be allowed to act on L-lysine. The method is normally preferably carried out in an aqueous medium, or a mixture of the aqueous medium and an organic solvent. The method of the present invention is more preferably carried out in the presence of ferrous ion.

Examples of the aqueous medium include water and buffers.

Examples of the organic solvent include those in which the reaction substrate is highly soluble, such as methanol, ethanol, 1-propanol, 2-propanol, 1-butanol, tert-butanol, acetone, and dimethyl sulfoxide. Other examples of the organic solvent include ethyl acetate, butyl acetate, toluene, chloroform, and n-hexane, which are effective for removal of reaction by-products and the like.

The reaction substrate L-lysine is usually used at a substrate concentration within the range of 0.01% w/v to 90% w/v, preferably 0.1% w/v to 30% w/v. The reaction substrate may be added at once when the reaction is started, but is preferably added continuously or intermittently in view of reducing an effect of substrate inhibition of the enzyme, if any, and increasing the concentration of the product accumulated.

The number of moles of the 2-oxoglutaric acid required for the reaction is normally equivalent to, or higher than, that of the substrate, preferably equivalent to, or up to 1.2-fold higher than, that of the substrate. The 2-oxoglutaric acid may be added at once when the reaction is started, but is preferably added continuously or intermittently in view of reducing an inhibitory action on the enzyme, if any, and increasing the concentration of the product accumulated. Alternatively, an inexpensive compound that can be metabolized by the host, such as glucose, may be added instead of 2-oxoglutaric acid to allow metabolism of the compound by the host, and 2-oxoglutaric acid produced during this process may be used for the reaction.

The production method of the present invention is preferably carried out in the presence of ferrous ion. The ferrous ion is preferably used within the range of usually 0.01 mM to 100 mM, preferably 0.1 mM to 10 mM. The ferrous ion may be added as iron sulfate or the like at once when the reaction is started. Further addition of the ferrous ion during the reaction is also effective when the ferrous ion added was oxidized into ferric ion, or decreased due to formation of precipitation. In cases where the L-lysine hydroxylase, cell containing the enzyme, processed product of the cell, and/or culture broth obtained by culturing the cell, in the present invention already contain(s) a sufficient amount of ferrous ion, the addition of the ion is not necessarily required.

The reaction is carried out at a reaction temperature of usually 4° C. to 60° C., preferably 10° C. to 45° C., at a pH of usually 3 to 11, preferably 5 to 8. The reaction time is usually about 1 hour to about 72 hours.

The amount of the cell and/or processed product of the cell to be added to the reaction mixture is as follows. In cases where the cell is added, the cell concentration is usually about 0.1% w/v to about 50% w/v, preferably 1% w/v to 20% w/v in terms of the wet cell weight, and, in cases where the processed product such as an enzyme is used, the specific activity of the enzyme is determined, and the processed product is added in an amount equivalent to the cell concentration described above.

The hydroxy-L-lysine produced by the production method of the present invention can be purified, after the reaction, by separating cells, proteins, and the like in the reaction mixture by centrifugation, membrane treatment, and/or the like, and then performing an appropriate combination of methods such as extraction with an organic solvent(s), for example, 1-butanol and/or tert-butanol; distillation; column chromatography using an ion-exchange resin(s), silica gel, and/or the like; isoelectric crystallization; and/or crystallization with monohydrochloride, dihydrochloride, and/or calcium salt.

<Method for Producing Hydroxy-L-Pipecolic Acid>

The hydroxy-L-lysine produced by the method for the present invention can be used for production of hydroxy-L-pipecolic acid.

Examples of the method for producing hydroxy-L-pipecolic acid from hydroxy-L-lysine include the 3 kinds of methods described below.

The first method of the present invention for producing hydroxy-L-pipecolic acid from hydroxy-L-lysine is as follows.

<I> A method for producing hydroxy-L-pipecolic acid, which method comprises:

allowing hydroxy-L-lysine to react with <I-1> at least one enzyme selected from the group consisting of L-amino acid oxidase, L-amino acid dehydrogenase, and L-amino acid transferase, or with <I-2> amino acid racemase and at least one enzyme selected from the group consisting of D-amino acid oxidase, D-amino acid dehydrogenase, and D-amino acid transferase, to produce a cyclic amino acid having a double bond at the 1-position represented by General Formula (II); and allowing N-methyl-L-amino acid dehydrogenase to act on the resulting cyclic amino acid having a double bond at the 1-position to produce hydroxy-L-pipecolic acid represented by the following General Formula (III):

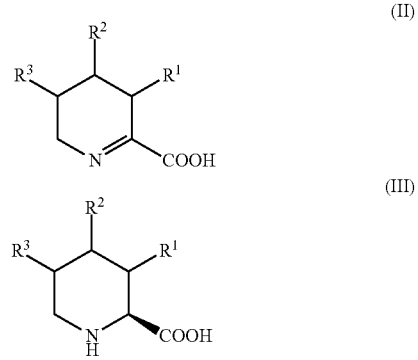

(wherein each of $R^1$, $R^2$ and $R^3$ represents a hydrogen atom or hydroxyl group, with the proviso that at least one of $R^1$, $R^2$ and $R^3$ represents a hydroxyl group).

The method is described below by way of exemplary schemes.

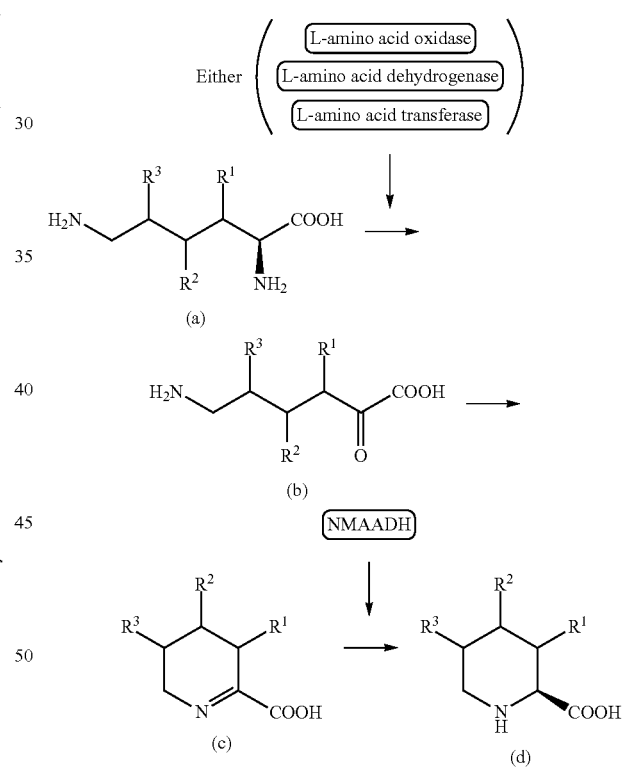

Scheme 1-1 uses N-methyl-L-amino acid dehydrogenase and at least one enzyme selected from the group consisting of L-amino acid oxidase, L-amino acid dehydrogenase, and L-amino acid transferase (wherein, in the formula, each of $R^1$, $R^2$ and $R^3$ represents a hydrogen atom or hydroxyl group, with the proviso that at least one of $R^1$, $R^2$ and $R^3$ represents a hydroxyl group).

First, using the enzyme(s) selected from the group consisting of L-amino acid oxidase, L-amino acid dehydrogenase, and L-amino acid transferase, the compound (a) (hydroxy-L-lysine) is converted to the compound (b). This is followed by spontaneous conversion of the compound (b) to the compound (c). Subsequently, the compound (c) is converted to the compound (d) (hydroxy-L-pipecolic acid) by N-methyl-L-amino acid dehydrogenase (NMAADH).

SEQ ID NO:24, and proteins comprising an amino acid sequence with an identity of not less than 80%, preferably not less than 90%, more preferably not less than 95% to SEQ ID NO:24, while retaining the activity.

Scheme 1-2

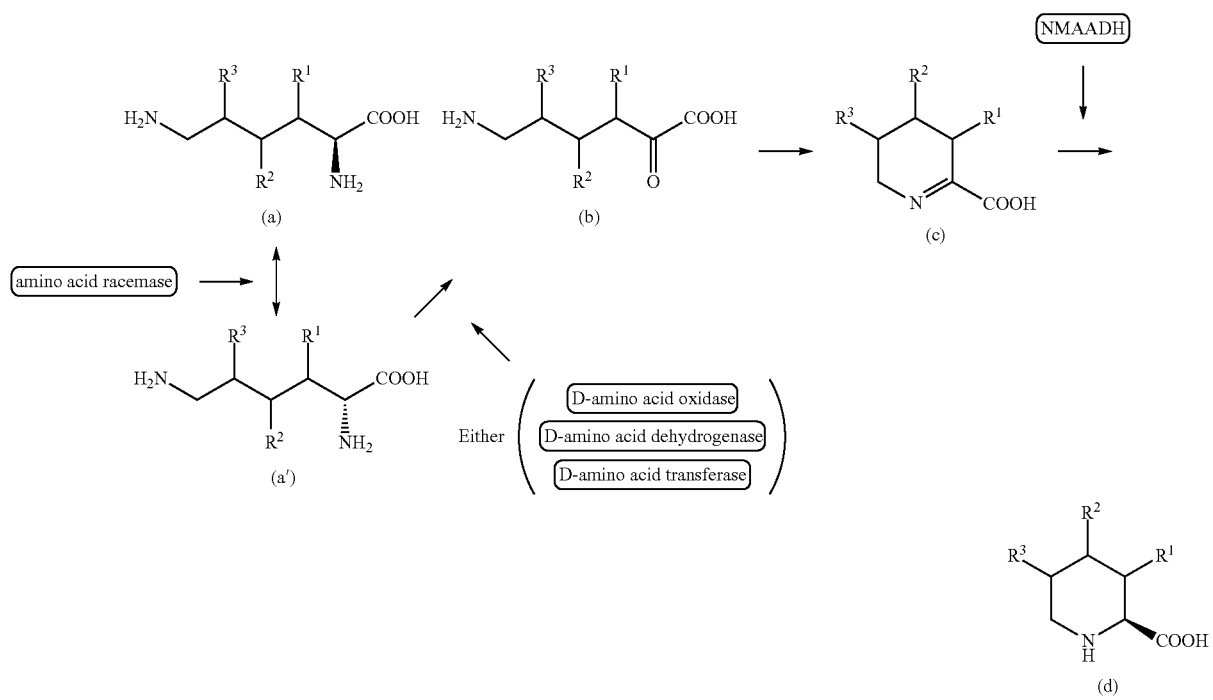

The L-amino acid oxidase herein is not limited as long as the L-amino acid oxidase can catalyze a reaction in which the amino group at the 2-position of hydroxy-L-lysine is converted to an oxo group. Examples of the L-amino acid oxidase include proteins comprising the amino acid sequence of SEQ ID NO:26, and proteins comprising an amino acid sequence with an identity of not less than 80%, preferably not less than 90%, more preferably not less than 95% to SEQ ID NO:26, while retaining the activity.

The L-amino acid dehydrogenase is not limited as long as the L-amino acid dehydrogenase can catalyze a reaction in which the amino group at the 2-position of hydroxy-L-lysine is converted to an oxo group. Examples of the L-amino acid dehydrogenase include the protein described in Nature, 1966, 211, 854.

The L-amino acid transferase (L-amino acid aminotransferase) is not limited as long as the L-amino acid transferase can catalyze a reaction in which the amino group at the 2-position of hydroxy-L-lysine is converted to an oxo group. Examples of the L-amino acid transferase include proteins comprising the amino acid sequence described in Eur. J. Biochem., 1998, 254, 347, and proteins comprising an amino acid sequence with an identity of not less than 80%, preferably not less than 90%, more preferably not less than 95% to the amino acid sequence, while retaining the activity.

The N-methyl-L-amino acid dehydrogenase is not limited as long as the N-methyl-L-amino acid dehydrogenase can catalyze a reaction in which the compound of General Formula (II) is converted to hydroxy-L-pipecolic acid. Examples of the N-methyl-L-amino acid dehydrogenase include proteins comprising the amino acid sequence of Scheme 1-2 uses amino acid racemase, N-methyl-L-amino acid dehydrogenase, and at least one enzyme selected from the group consisting of D-amino acid oxidase, D-amino acid dehydrogenase, and D-amino acid transferase (wherein, in the formula, each of $R^1$, $R^2$ and $R^3$ represents a hydrogen atom or hydroxyl group, with the proviso that at least one of $R^1$, $R^2$ and $R^3$ represents a hydroxyl group).

First, the compound (a) (hydroxy-L-lysine) is converted to the D-isomer compound (a') (hydroxy-D-lysine) by amino acid racemase, and the compound (a') is then converted to the compound (b) by an enzyme(s) selected from the group consisting of D-amino acid oxidase, D-amino acid dehydrogenase, and D-amino acid transferase. This is followed by spontaneous conversion of the compound (b) to the compound (c). The compound (c) is then converted to the compound (d) (hydroxy-L-pipecolic acid) by N-methyl-L-amino acid dehydrogenase (NMAADH).

The amino acid racemase is not limited as long as the amino acid racemase can catalyze a reaction in which hydroxy-L-lysine is converted to hydroxy-D-lysine. Examples of the amino acid racemase include proteins comprising the amino acid sequence of SEQ ID NO:30, and proteins comprising an amino acid sequence with an identity of not less than 80%, preferably not less than 90%, more preferably not less than 95% to SEQ ID NO:30, while retaining the activity.

The D-amino acid oxidase is not limited as long as the D-amino acid oxidase can catalyze a reaction in which amino group at the 2-position of hydroxy-D-lysine is converted to an oxo group. Examples of the D-amino acid oxidase include proteins comprising the amino acid sequence described in Biochemistry, 2005, 70, 40, and proteins comprising an amino acid sequence with an identity of not less than 80%, preferably not less than 90%, more preferably not less than 95% to the amino acid sequence, while retaining the activity.

The D-amino acid dehydrogenase is not limited as long as the D-amino acid dehydrogenase can catalyze a reaction in which the amino group at the 2-position of hydroxy-D-lysine is converted to an oxo group. Examples of the D-amino acid dehydrogenase include DauA described in Microbiology, 2010, 156(Pt 1), 60 and Proc. Natl. Acad. Sci. U.S.A., 2009, 106, 906, and proteins comprising an amino acid sequence with an identity of not less than 80%, preferably not less than 90%, more preferably not less than 95% to the amino acid sequence of DauA, while retaining the activity.

The D-amino acid transferase (D-amino acid aminotransferase) is not limited as long as the D-amino acid transferase can catalyze a reaction in which the amino group at the 2-position of hydroxy-D-lysine is converted to an oxo group. Examples of the D-amino acid transferase include D-AAT described in Protein Eng, 1998, 11, 53, and proteins comprising an amino acid sequence with an identity of not less than 80%, preferably not less than 90%, more preferably not less than 95% to D-AAT, while retaining the activity.

The N-methyl-L-amino acid dehydrogenase is not limited as long as the N-methyl-L-amino acid dehydrogenase catalyzes a reaction in which the compound of General Formula (II) is converted to hydroxy-L-pipecolic acid. Examples of the N-methyl-L-amino acid dehydrogenase include proteins comprising the amino acid sequence of SEQ ID NO:24, and proteins comprising an amino acid sequence with an identity of not less than 80%, preferably not less than 90%, more preferably not less than 95% to SEQ ID NO:24, while retaining the activity.

In each of Scheme 1-1 and Scheme 1-2, the enzymatic reactions may be carried out separately, but the reactions are preferably carried out continuously in a single reaction system.

More preferably, the reactions are carried out by allowing cells containing the enzymes which catalyze the reactions to react with hydroxy-L-lysine. Although the cells containing the enzymes which catalyze the reactions may be microorganism cells intrinsically having these enzymes, it is preferred to use cells transformed with DNA encoding the enzymes. In Scheme 1-1, the cells to be used are preferably cells transformed with DNA encoding at least one enzyme selected from the group consisting of L-amino acid oxidase, L-amino acid dehydrogenase, and L-amino acid transferase, and DNA encoding N-methyl-L-amino acid dehydrogenase. In Scheme 1-2, the cells to be used are preferably cells transformed with DNA encoding at least one enzyme selected from the group consisting of D-amino acid oxidase, D-amino acid dehydrogenase, and D-amino acid transferase, DNA encoding amino acid racemase, and DNA encoding N-methyl-L-amino acid dehydrogenase.

The cells may be prepared by incorporating each of these DNAs into the chromosome; by introducing these DNAs into a single vector and then transforming the host with the single vector; or by separately introducing the DNAs into vectors and then transforming the host with these vectors.

The method for transformation of the host cells such as microorganism cells, the type of the host, and the like are the same as those described in the 2-oxoglutarate-dependent L-lysine hydroxylase section.

Since N-methyl-L-amino acid dehydrogenase requires NAD(P)H as a co-enzyme, an NAD(P)H-regenerating system is preferably allowed to coexist. That is, in cases where the NAD(P)H is added, NAD(P)$^+$ generated from the NAD(P)H is preferably regenerated into NAD(P)H from the viewpoint of increasing the production efficiency. Examples of the regeneration method include: 1) a method in which the NAD(P)$^+$-reducing capacity of the host microorganism itself is used; 2) a method in which a microorganism(s) having a capacity to generate NAD(P)H from NAD(P)$^+$, a processed product(s) thereof, and/or an enzyme (s) (regenerating enzyme(s)) which can be used for regeneration of NAD(P)H, such as glucose dehydrogenase, formate dehydrogenase, alcohol dehydrogenase, amino acid dehydrogenase, and/or organic acid dehydrogenase (for example, malate dehydrogenase), is/are added to the reaction system; and 3) a method in which, in production of the transformant, one or more of the genes of the regenerating enzymes which can be used for the regeneration of NAD(P)H is introduced into the host together with the DNA in the present invention.

In particular, in the method 1), glucose, ethanol, formic acid, and/or the like is/are preferably added to the reaction system.

Examples of microorganisms/processed products/enzymes which may be used in the method 2) include microorganisms containing the regenerating enzymes; processed products of these microorganisms such as acetone-treated products, lyophilized products, and physically or enzymatically disrupted products; fractions of the enzymes extracted as crude products or purified products; and products prepared by immobilizing any of these products on a carrier such as polyacrylamide gel, carrageenan gel, or the like. Alternatively, a commercially available enzyme(s) may be used. In such cases, addition of one or more of compounds to be used as substrates for the regenerating enzymes, such as glucose in cases of use of glucose dehydrogenase, formic acid in cases of use of formate dehydrogenase, and ethanol or isopropanol in cases of use of alcohol dehydrogenase, is necessary.

In cases where the reactions of Scheme 1-1 or Scheme 1-2 are continuously carried out in a single reaction system, the scheme is preferably carried out in an aqueous medium or a mixture of the aqueous medium and an organic solvent(s) containing hydroxy-L-lysine, cells transformed with genes encoding the enzymes, a processed product of the transformed cells, and/or a culture broth obtained by culturing the transformed cells.

Examples of the aqueous medium include water and buffers. Examples of the organic solvent include those in which the reaction substrate is highly soluble, such as methanol, ethanol, 1-propanol, 2-propanol, 1-butanol, tert-butanol, acetone, and dimethyl sulfoxide. Other examples of the organic solvent include ethyl acetate, butyl acetate, toluene, chloroform, and n-hexane, which are effective for removal of reaction by-products and the like.

The reaction substrate hydroxy-L-lysine is usually used at a substrate concentration within the range of 0.01% w/v to 90% w/v, preferably 0.1% w/v to 30% w/v. The reaction substrate may be added at once when the reaction is started, but is preferably added continuously or intermittently in view of reducing an effect of substrate inhibition of the enzyme, if any, and increasing the concentration of the product accumulated.

If necessary, a coenzyme(s) such as NAD(P)H is/are normally added at 0.001 mM to 100 mM, preferably 0.01 mM to 10 mM.

The reaction is carried out at a reaction temperature of usually 4° C. to 60° C., preferably 10° C. to 45° C., at a pH of usually 3 to 11, preferably 5 to 8. The reaction time is usually about 1 hour to about 72 hours.

The hydroxy-L-pipecolic acid produced by the method of the present invention can be purified, after the reaction, by separating cells and proteins in the reaction mixture by centrifugation, membrane treatment, and/or the like, and then performing an appropriate combination of methods such as extraction with an organic solvent(s), for example, 1-butanol and/or tert-butanol; distillation; column chromatography using an ion-exchange resin(s), silica gel, and/or the like; isoelectric crystallization; and/or crystallization with monohydrochloride, dihydrochloride, and/or calcium salt.

The second method of the present invention for producing hydroxy-L-pipecolic acid from hydroxy-L-lysine is as follows.

<II> A method for producing hydroxy-L-pipecolic acid, which method comprises:

allowing hydroxy-L-lysine to react with at least one enzyme selected from the group consisting of L-lysine 6-oxidase, L-lysine 6-dehydrogenase, and L-lysine 6-transferase to produce a cyclic amino acid having a double bond at the 6-position represented by General Formula (IV); and allowing pyrroline-5-carboxylate reductase to act on the resulting cyclic amino acid having a double bond at the 6-position to produce hydroxy-L-pipecolic acid represented by General Formula (III):

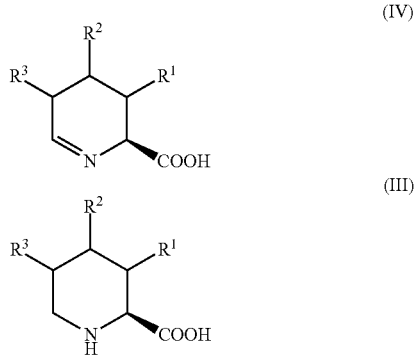

(wherein each of $R^1$, $R^2$ and $R^3$ represents a hydrogen atom or hydroxyl group, with the proviso that at least one of $R^1$, $R^2$ and $R^3$ represents a hydroxyl group).

The method is described below by way of an exemplary scheme (in the formula, each of $R^1$, $R^2$ and $R^3$ represents a hydrogen atom or hydroxyl group, with the proviso that at least one of $R^1$, $R^2$ and $R^3$ represents a hydroxyl group).

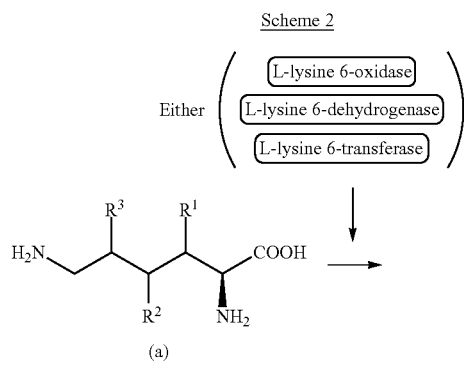

Scheme 2

First, the compound (a) (hydroxy-L-lysine) is converted to the compound (b') by at least one enzyme selected from the group consisting of L-lysine 6-oxidase, L-lysine 6-dehydrogenase, and L-lysine 6-transferase, and this is followed by spontaneous conversion of the compound (b') to the compound (c'). The compound (c') is then converted to the compound (d) (hydroxy-L-pipecolic acid) by pyrroline-5-carboxylate (P5C) reductase.

The L-lysine 6-oxidase is not limited as long as the L-lysine 6-oxidase can catalyze a reaction in which the amino group at the 6-position of hydroxy-L-lysine is converted to an oxo group. Examples of the L-lysine 6-oxidase include proteins comprising the amino acid sequence of IodA described in Biochim. Biophys. Acta., 2006, 1764 1577, and proteins comprising an amino acid sequence with an identity of not less than 80%, preferably not less than 90%, more preferably not less than 95% to the amino acid sequence of IodA, while retaining the activity.

The L-lysine 6-dehydrogenase is not limited as long as the L-lysine 6-dehydrogenase can catalyze a reaction in which the amino group at the 6-position of hydroxy-L-lysine is converted to an oxo group. Examples of the L-lysine 6-dehydrogenase include proteins comprising the amino acid sequence described in J. Biochem., 105, 1002-1008 (1989), and proteins comprising an amino acid sequence with an identity of not less than 80%, preferably not less than 90%, more preferably not less than 95% to the amino acid sequence, while retaining the activity.

The L-lysine 6-transferase (lysine-6-aminotransferase) is not limited as long as the L-lysine 6-transferase can catalyze a reaction in which the amino group at the 6-position of hydroxy-L-lysine is converted to an oxo group. Examples of the L-lysine 6-transferase include proteins comprising the amino acid sequence described in WO 2001/048216, and proteins comprising an amino acid sequence with an identity of not less than 80%, preferably not less than 90%, more preferably not less than 95% to the amino acid sequence, while retaining the activity.

The pyrroline-5-carboxylate (P5C) reductase is not limited as long as the pyrroline-5-carboxylate reductase can catalyze a reaction in which the compound represented by General Formula (IV) is converted to hydroxy-L-pipecolic acid represented by General Formula (III). Examples of the pyrroline-5-carboxylate reductase include proteins comprising the amino acid sequence described in WO 2001/048216, and proteins comprising an amino acid sequence with an identity of not less than 80%, preferably not less than 90%, more preferably not less than 95% to the amino acid sequence, while retaining the activity Although the enzymatic reactions in Scheme 2 may be carried out separately, the reactions are preferably carried out continuously in a single reaction system.

More preferably, the reactions are carried out by allowing cells containing the enzymes which catalyze the reactions to react with hydroxy-L-lysine. Although the cells containing the enzymes which catalyze the reactions may be cells intrinsically having these enzymes, it is preferred to use cells transformed with DNA encoding the enzymes. More specifically, it is preferred to use cells transformed with DNA encoding at least one enzyme selected from the group consisting of L-lysine 6-oxidase, L-lysine 6-dehydrogenase, and L-lysine 6-transferase, and DNA encoding pyrroline-5-carboxylate (P5C) reductase.

The method for transformation of the host cells such as microorganism cells, the type of the host, and the like are the same as those described in the 2-oxoglutarate-dependent L-lysine hydroxylase section.

In cases where the reactions of Scheme 2 are continuously carried out in a single reaction system, the scheme is preferably carried out in an aqueous medium or a mixture of the aqueous medium and an organic solvent(s), containing hydroxy-L-lysine, cells transformed with genes encoding the enzymes, a processed product of the transformed cells, and/or a culture broth obtained by culturing the transformed cells.

The reaction conditions, addition and regeneration of co-enzyme, and the method of recovery of hydroxy-L-pipecolic acid are the same as those described in the section <I>.

The third method of the present invention for producing hydroxy-L-pipecolic acid from hydroxy-L-lysine is as follows.

<III> A method for producing hydroxy-L-pipecolic acid, which method comprises allowing lysine cyclodeaminase to act on hydroxy-L-lysine to produce hydroxy-L-pipecolic acid represented by General Formula (III).

The lysine cyclodeaminase is not limited as long as the lysine cyclodeaminase can catalyze a reaction in which hydroxy-L-lysine is converted to hydroxy-L-pipecolic acid. Examples of the lysine cyclodeaminase include proteins comprising the amino acid sequence described in Biochimie 2007, 89, 591, and proteins comprising an amino acid sequence with an identity of not less than 80%, preferably not less than 90%, more preferably not less than 95% to the amino acid sequence, while retaining the activity.

The reaction by lysine cyclodeaminase is preferably carried out by allowing cells containing lysine cyclodeaminase to react with hydroxy-L-lysine. Although the microorganism containing lysine cyclodeaminase may be cells intrinsically having the enzyme, it is preferred to use cells transformed with DNA encoding lysine cyclodeaminase.

The method for transformation of the host cells such as microorganism cells, the type of the host, and the like are the same as those described in the 2-oxoglutarate-dependent L-lysine hydroxylase section.

In cases where the reaction of converting hydroxy-L-lysine to hydroxy-L-pipecolic acid by lysine cyclodeaminase is carried out, the reaction is preferably carried out in an aqueous medium or a mixture of the aqueous medium and an organic solvent(s), containing hydroxy-L-lysine, cells transformed with DNA encoding lysine cyclodeaminase, a processed product of the transformed cells, and/or a culture broth obtained by culturing the transformed cells.

The reaction conditions, addition and regeneration of co-enzyme, and the method of recovery of hydroxy-L-pipecolic acid are the same as those described in the section <I>.

It is also possible to produce hydroxy-L-pipecolic acid directly from L-lysine using, at once, 2-oxoglutarate-dependent L-lysine hydroxylase and an enzyme(s) which convert(s) hydroxy-L-lysine to hydroxy-L-pipecolic acid. However, since the enzyme(s) which convert(s) hydroxy-L-lysine to hydroxy-L-pipecolic acid may act on L-lysine to cause by-production of L-pipecolic acid before the 2-oxoglutarate-dependent L-lysine hydroxylase acts on L-lysine, the enzyme(s) which convert(s) hydroxy-L-lysine to hydroxy-L-pipecolic acid need(s) to be an enzyme(s) which preferentially act(s) on hydroxy-L-lysine rather than L-lysine. In such cases, the host cells may be transformed at once with DNA for 2-oxoglutarate-dependent L-lysine hydroxylase and DNA for the enzyme(s) which convert(s) hydroxy-L-lysine to hydroxy-L-pipecolic acid.

In cases where hydroxy-L-lysine produced by the method of the present invention is used for production of hydroxy-L-pipecolic acid, purification of the hydroxy-L-lysine may be omitted, and the only purification to be carried out may be purification after the conversion to hydroxy-L-pipecolic acid.

EXAMPLES

The present invention is described below in more detail by way of Examples, but the present invention is not limited by these.

Example 1

Cloning of 2-oxoglutarate-dependent L-lysine Hydroxylase Gene

Based on a gene sequence (hyl-1, SEQ ID NO:1) encoding an L-arginine-β hydroxylase VioC homologue Hyl-1 derived from the *Flavobacterium johnsoniae* NBRC14942 strain (GenBank Accession No. ABQ06186, SEQ ID NO:2), primers for amplifying the full-length sequence of the hyl-1 gene, hyl1_F (SEQ ID NO:13) and hyl1_R (SEQ ID NO:14), were designed and synthesized. Using chromosomal DNA of *Flavobacterium johnsoniae* as a template, PCR was carried out according to a conventional method, to obtain a DNA fragment of about 1.0 kbp.

In addition, VioC homologues derived from the *Kineococcus radiotolerans* NBRC101839 strain, *Chitinophaga pinensis* NBRC15968 strain, *Chryseobacterium gleum* NBRC15054 strain, and *Niastella koreensis* NBRC106392 strain were designated Hyl-2 (GenBank Accession No. ABS05421, SEQ ID NO:4), Hyl-3 (GenBank Accession No. ACU60313, SEQ ID NO:6), Hyl-4 (GenBank Accession No. EFK34737, SEQ ID NO:8), and Hyl-5 (GenBank Accession No. AEV99100, SEQ ID NO:10), respectively. Based on gene sequences encoding the enzymes, (hyl-2 (SEQ ID NO:3), hyl-3 (SEQ ID NO:5), hyl-4 (SEQ ID NO:7), and hyl-5 (SEQ ID NO:9)), primers for amplifying the full-length sequence of each gene were designed and synthesized. Primers hyl2_f (SEQ ID NO:15) and hyl2_r (SEQ ID NO:16) for hyl-2, primers hyl3_f (SEQ ID NO:17) and hyl3_r (SEQ ID NO:18) for hyl-3, primers hyl4_f (SEQ ID NO:19) and hyl4_r (SEQ ID NO:20) for hyl-4, and primers hyl5f (SEQ ID NO:21) and hyl5_r (SEQ ID NO:22) for hyl-5 were synthesized, and PCR was carried out using chromosomal DNA of each strain as a template according to a conventional method. Each reaction produced a DNA fragment of about 1.0 kbp.

Each of the 5 kinds of DNA fragments obtained was digested with restriction enzymes NdeI and XhoI, and ligated into NdeI/XhoI-digested pET21a (Novagen) according to a conventional method, to obtain pEHYL1, pEHYL2, pEHYL3, pEHYL4, and pEHYL5, respectively.

A gene sequence (hyl-6, SEQ ID NO:11) encoding Hyl-6 (GenBank Accession No. EAR24255, SEQ ID NO:12), which was derived from a marine actinobacterium PHSC20C1, was artificially synthesized by DNA2.0, Inc., and inserted into pJExpress401 (DNA2.0) to prepare a plasmid pJHYL6.

Subsequently, E. coli (Eschelichia coli) BL21(DE3) (manufactured by Invitrogen) was transformed with each of the resulting plasmids according to a conventional method, to obtain recombinant E. coli BL21(DE3)/pEHYL1, BL21 (DE3)/pEHYL2, BL21(DE3)/pEHYL3, BL21(DE3)/pEHYL4, BL21(DE3)/pEHYL5, and BL21(DE3)/pJHYL6. In order to obtain bacterial cells expressing the introduced genes, each type of recombinant E. coli was cultured at 30° C. using liquid LB medium supplemented with ampicillin and a lac promoter inducer, and collected at Hour 20 of the culture.

Example 2

Figure 2:
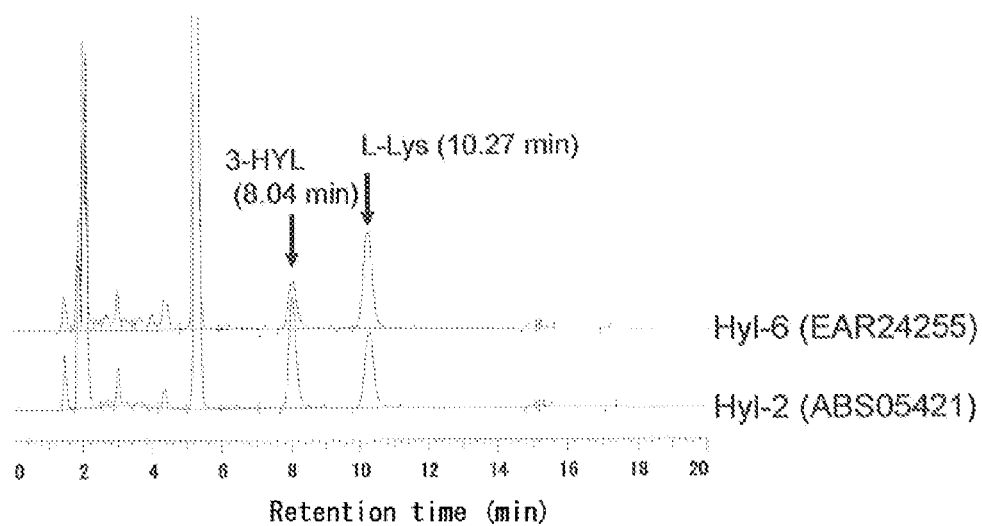
FIG. 2 is a diagram illustrating conversion of L-lysine to 3-hydroxylysine by Hyl-2 or 6.

Confirmation of 2-Oxoglutarate-Dependent L-Lysine Hydroxylase Activity by Resting-Cell Reaction In a plastic tube, 5 mM L-lysine, 10 mM 2-oxoglutaric acid, 1 mM L-ascorbic acid, 0.1 mM iron sulfate, and recombinant E. coli obtained by the method according to Example 1 were mixed to provide a reaction mixture such that the turbidity OD600 was 10. The reaction was allowed to proceed in 0.5 ml of the prepared mixture at 30° C. at pH 7.0 for 3 hours. The reaction product was derivatized with 1-fluoro-2,4-dinitrophenyl-5-L-alaninamide (FDAA), and then analyzed by HPLC. As a result, as shown in FIG. 1 and FIG. 2, it could be confirmed that BL21(DE3)/pEHYL2 and BL21(DE3)/pJHYL6 produced a compound corresponding to the retention time of a standard product of 3-hydroxylysine, 8.04 minutes. It could also be confirmed that BL21 (DE3)/pEHYL1, BL21(DE3)/pEHYL3, BL21(DE3)/pEHYL4, and BL21(DE3)/pEHYL5 produced a compound corresponding to the retention time of a standard product of 4-hydroxylysine, 8.16 minutes.

The conditions for analyzing the hydroxylysine by HPLC were as follows.

Column, COSMOSIL 5C18-AR-II (4.6 mm×150 mm), manufactured by Nacalai Tesque, Inc.; mobile phase, 50 mM phosphate buffer (pH 2.7); flow rate, 1.0 mL/minute; column temperature, 40° C.; and UV, 340 nm.

Example 3

Synthesis of (2S,3S)-3-Hydroxylysine

In a 1-L jar fermenter, 35 mL of 1 M potassium phosphate buffer (pH 7.0), 304 mL of desalted water, 1.28 g of L-lysine hydrochloride, 2.05 g of 2-oxoglutaric acid, 0.14 g of sodium L-ascorbate, 0.02 g of iron sulfate, 0.35 g of Adekanol LG109, and 8 g of wet cells of recombinant E. coli BL21(DE3)/pEHYL2 obtained by the method according to Example 1 were mixed together, and the reaction was allowed to proceed at 30° C., pH 7.0, a stirring rate of 500 rpm, and an aeration rate of 2.0 vvm for 17 hours. Completion of the reaction was judged by confirming disappearance of the peak for L-lysine by HPLC analysis. From the liquid after the completion of the reaction, bacterial cells and bacterial debris were removed by centrifugation and microfiltration, to obtain 390 g of a filtrate.

The conditions for analyzing the L-lysine by HPLC were as follows.

Column, SUMICHIRAL OA-6100 (4.6 mm×250 mm), manufactured by Sumika Chemical Analysis Service, Ltd.; mobile phase, 1 mM copper sulfate; flow rate, 1.0 mL/minute; column temperature, 30° C.; and UV, 254 nm.

After passing 390 g of the filtrate through an ion-exchange resin column (DIAION (registered trademark) SK-1B (Type H), 60.0 g), washing was carried out with water, followed by elution with an aqueous solution containing 150 mmol ammonia. The ammonia eluate was concentrated to obtain 1.0 g of (2S,3S)-3-hydroxylysine (6.17 mmol; yield, 88%).

The results of measurement of physical properties of the resulting (2S,3S)-3-hydroxylysine were as follows.

$^1$H-NMR (400 MHz, D$_2$O) δ, 1.45-1.58 (2H, m), 1.63-1.73 (1H, m), 1.74-1.88 (1H, m), 2.93-3.04 (2H, m), 3.47 (1H, d, J=4.3 Hz), 3.89 (1H, dt, J=8.4, 4.5 Hz)

Example 4

Determination of Stereochemistry of ($2^S,3^S$)-3-Hydroxylysine

In a flask, 8.3 mg (0.051 mmol) of (2S,3S)-3-hydroxylysine obtained by the method according to Example 3, 0.26 ml of 1 mol/L aqueous sodium hydroxide solution, and 18 μl (0.13 mmol) of benzyloxycarbonyl chloride were placed, and the resulting mixture was stirred at room temperature for 1 hour. To the mixture, 0.26 ml of 1 mol/L aqueous sodium hydroxide solution and 18 μl (0.13 mmol) of benzyloxycarbonyl chloride were further added, and the reaction was allowed to proceed overnight at room temperature. Subsequently, 0.5 ml of tetrahydrofuran was added to the reaction mixture, and the reaction was allowed to proceed at 60° C. for additional 2 hours. After cooling the reaction mixture to room temperature, 95 mg of sodium hydroxide was added thereto, and the reaction was allowed to proceed at room temperature overnight. The reaction mixture was washed twice with toluene-tetrahydrofuran (1:1), and 250 μl of concentrated hydrochloric acid was added to the reaction mixture to make the reaction mixture strongly acidic. After 3 times of washing with ethyl acetate, the aqueous layer was subjected to 4 times of extraction with 1-butanol. The 1-butanol layer was dried over anhydrous magnesium sulfate, and then concentrated, to obtain 14.6 mg of (4S,5S)-5-(3-benzyloxycarbonylaminopropyl)-2-oxo-4-oxazolidinecarboxylic acid (0.045 mmol; yield, 89%).

The results of NOESY measurement are shown in the following formula. Since a cross peak was found between the 3-position hydrogen atom (H4) and 4-position hydrogen atom (H5), but was not found between the 4-position and the 1'-position, the substituents at the 4-position and the 5-position could be confirmed to have the cis configuration. Since the absolute configuration of the lysine used in the enzymatic reaction was S, it could be confirmed that the 5-(3-benzyloxycarbonylaminopropyl)-2-oxo-4-oxazolidinecarboxylic acid obtained in the present Example has the stereochemistry of (4S,5S), and that 3-hydroxylysine as its material has the stereochemistry of (2S,3S).

The results of measurement of physical properties of the resulting (4S,5S)-5-(3-benzyloxycarbonylaminopropyl)-2-oxo-4-oxazolidinecarboxylic acid were as follows.

$^1$H-NMR (400 MHz, MeOH-d$_4$) δ, 1.39-1.53 (3H, m, H$^{1'}$, H$^{2'}$×2), 1.59-1.68 (1H, m, H$^{1'}$), 3.02-3.08 (2H, m, H$^{3'}$), 3.60-3.64 (1H, m, H$^4$), 3.93-4.00 (1H, m, H$^5$), 4.90-5.02 (2H, m, Bn), 7.18-7.28 (5H, m, Bn).

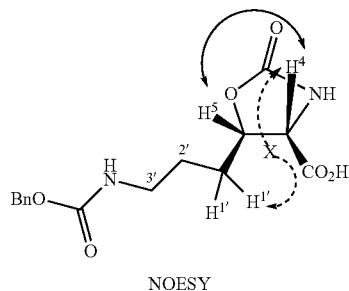

NOESY

Reference Example 1

[Preparation Example of Recombinant E. coli JM109/pKW32 (dpkA, aip, gdh, kr), in which N-Methyl-L-amino Acid Dehydrogenase (Hereinafter Referred to as DpkA), L-Amino Acid Oxidase (Hereinafter Referred to as AlP), Glucose-1-dehydrogenase (Hereinafter Referred to as GDH), and Amino Acid Racemase (hereinafter referred to as KR) Are Co-expressed]

(1) Cloning of Genes

Based on a gene sequence (hereinafter referred to as dpkA, SEQ ID NO:23) encoding DpkA derived from *Pseudomonas putida* (GenBank Accession No. BAD89743, SEQ ID NO:24), primers for amplifying the full-length sequence of the dpkA gene, dpkA_F (SEQ ID NO:31) and dpkA_R (SEQ ID NO:32), were designed and synthesized. PCR was carried out using chromosomal DNA of *Pseudomonas putida* as a template according to a conventional method, to obtain a DNA fragment of about 1.0 kbp.

A gene sequence (hereinafter referred to as aip, SEQ ID NO:25) encoding a protein AlP (SEQ ID NO:26), which has the same sequence as the sequence of *Scomber japonicus*-derived L-amino acid oxidase (GenBank Accession No. CAC00499) except that the signal peptide is removed and methionine is added, was designed and artificially synthesized. Primers for amplifying the full-length sequence of the aip gene, aip_F (SEQ ID NO:33) and aip_R (SEQ ID NO:34), were designed and synthesized. PCR was carried out according to a conventional method, to obtain a DNA fragment of about 1.5 kbp.

Based on a gene sequence (hereinafter referred to as gdh, SEQ ID NO:27) encoding a protein (SEQ ID NO:28) comprising the sequence of *Bacillus subtilis*-derived GDH (GenBank Accession No. NP_388275) except that the 96th amino acid residue glutamic acid is substituted with alanine, primers for amplifying the full-length sequence of the gdh gene, gdh_F (SEQ ID NO:35) and gdh_R (SEQ ID NO:36), were designed and synthesized.

PCR was carried out according to a conventional method, to obtain a DNA fragment of about 0.8 kbp.

Based on a gene sequence (hereinafter referred to as kr, SEQ ID NO:29) encoding KR derived from *Pseudomonas putida* (GenBank Accession No. NP_745855, SEQ ID NO:30), primers for amplifying the full-length sequence of the kr gene, kr_F (SEQ ID NO:37) and kr_R (SEQ ID NO:38), were designed and synthesized. PCR was carried out using chromosomal DNA of *Pseudomonas putida* as a template according to a conventional method, to obtain a DNA fragment of about 1.2 kbp.

(2) Preparation of Expression Plasmid

Each of the DNA fragments obtained in (1) was digested with restriction enzymes EcoRI and XbaI, and introduced downstream of the trc promoter in a MunI/XbaI digest of a plasmid pKW32, which is described in WO 2012/029819, using a Ligation-Convenience Kit (manufactured by Nippon Gene Co., Ltd.), to obtain pKW32dpkA, pKW32aip, pKW32gdh, and pKW32kr, respectively.

Subsequently, pKW32aip was digested with SpeI and NdeI to obtain a DNA fragment of about 2.4 kbp containing aip, and the resulting DNA fragment was introduced downstream of dpkA in the linear plasmid of about 4.2 kbp obtained by digesting pKW32dpkA with XbaI and NdeI, to obtain pKW32 (dpkA, aip).

pKW32gdh was digested with SpeI and NdeI to obtain a DNA fragment of about 1.7 kbp containing gdh, and the resulting DNA fragment was introduced downstream of aip in the linear plasmid of about 5.7 kbp obtained by digesting pKW32 (dpkA, aip) with XbaI and NdeI, to obtain pKW32 (dpkA, aip, gdh).

Finally, pKW32kr was digested with SpeI and NdeI to obtain a DNA fragment of about 2.1 kbp containing kr, and the resulting DNA fragment was introduced downstream of gdh in the linear plasmid of about 6.5 kbp obtained by digesting pKW32 (dpkA, aip, gdh) with XbaI and NdeI, to obtain pKW32 (dpkA, aip, gdh, kr).

(3) Preparation of Expressing Strain

Using the plasmid pKW32 (dpkA, aip, gdh, kr) obtained in (2), *E. coli* (*Escherichia coli*) JM109 (manufactured by Takara Bio Inc.) was transformed according to a conventional method, to obtain recombinant *E. coli* JM109/pKW32 (dpkA, aip, gdh, kr).

Example 5

Production of (2S,3S)-3-Hydroxypipecolic Acid

In a plastic tube, 0.75 mL of 1 M tris hydroxymethyl aminomethane buffer (pH 8.0), 9.21 mL of desalted water, 86 mg of the (2S,3S)-3-hydroxylysine obtained in Example 3, 0.083 ml of 50 mM NADPH, 0.7 ml of 1.0 M glucose, and 1.25 ml of a 100-g/L suspension of the recombinant *E. coli* JM109/pKW32 (dpkA, aip, gdh, kr) obtained in Reference Example 1 were mixed together, and the reaction was allowed to proceed at 30° C. at pH 8.0 at a stirring rate of 1000 rpm for 20 hours. Completion of the reaction was judged by confirming disappearance of the peak for (2S,3S)-3-hydroxylysine by HPLC analysis. From the liquid after the completion of the reaction, bacterial cells and bacterial debris were removed by centrifugation, to obtain 10.5 g of a supernatant.

The conditions for analyzing the (2S,3S)-3-hydroxylysine by HPLC were as follows.

Column, CLC-D (4.6 mm×150 mm), manufactured by SUPELCO; mobile phase, 2 mM copper sulfate; flow rate, 1.0 mL/minute; column temperature, 30° C.; and UV, 254 nm.

After passing 10.5 g of the supernatant through an ion-exchange resin column (DIAION (registered trademark) SK-1B (Type H), 4.0 g), washing was carried out with water, followed by elution with an aqueous solution containing 16.4 mmol ammonia. The ammonia eluate was concentrated to obtain 255 mg of a solid brown substance. As a result of NMR analysis, this solid substance was found to be a mixture containing 20 wt % (2S,3R)-3-hydroxypipecolic acid (0.35 mmol; yield, 66.3%) and 80 wt % tris hydroxymethyl aminomethane.

The results of measurement of physical properties of the resulting solid substance were as follows.

$^1$H-NMR (400 MHz, D$_2$O) δ, 1.38-1.56 (2H, m), 1.73-1.85 (2H, m), 2.71-2.79 (1H, m), 3.04-3.11 (1H, m), 3.23 (1H, d, J=7.6 Hz), 3.79-3.86 (1H, m).

Example 6

Synthesis of (2S,4R)-4-Hydroxylysine

In a 1-L jar fermenter, 335 mL of desalted water, 1.28 g of L-lysine hydrochloride, 2.05 g of 2-oxoglutaric acid, 0.14 g of sodium L-ascorbate, 0.02 g of iron sulfate, 0.35 g of Adekanol LG109, and 8 g of wet cells of recombinant E. coli BL21(DE3)/pEHYL1 obtained by the method according to Example 1 were mixed together, and the reaction was allowed to proceed at 30° C., pH 6.8, a stirring rate of 500 rpm, and an aeration rate of 2.0 vvm for 19 hours. Completion of the reaction was judged by confirming disappearance of the peak for L-lysine by HPLC analysis. From the liquid after the completion of the reaction, bacterial cells and bacterial debris were removed by centrifugation and microfiltration, to obtain 345 g of a filtrate.

The conditions for analyzing the L-lysine by HPLC were as follows.

Column, SUMICHIRAL OA-6100 (4.6 mm×250 mm), manufactured by Sumika Chemical Analysis Service, Ltd.; mobile phase, 1 mM copper sulfate; flow rate, 1.0 mL/minute; column temperature, 30° C.; and UV, 254 nm.

After passing 345 g of the resulting filtrate through an ion-exchange resin column (DIAION (registered trademark) SK-1B (Type H), 40.0 g) replaced with NH3, washing was carried out with water, followed by elution with an aqueous solution containing 64 mmol ammonia. The ammonia eluate was concentrated to obtain 1.1 g of (2S,4R)-4-hydroxylysine (6.79 mmol; yield, 97%).

The results of measurement of physical properties of the resulting (2S,4R)-4-hydroxylysine were as follows.

$^1$H-NMR (400 MHz, D$_2$O) δ, 1.50-1.65 (3H, m), 1.71 (1H, ddd, J=14.4, 9.1, 4.3 Hz), 2.62-2.75 (2H, m), 3.32 (1H, dd, J=8.6, 4.8 Hz), 3.72-3.80 (1H, m).

Example 7

Determination of Stereochemistry of (2S,4R)-4-Hydroxylysine

In a flask, 47 mg (0.30 mmol) of (2S,4R)-4-hydroxylysine obtained in Example 6, 0.2 ml of water, and 0.2 ml of 6 N hydrochloric acid were placed, and the reaction was allowed to proceed at room temperature for 1 hour. The reaction mixture was concentrated to obtain 67 mg of crude (3S,5R)-3-amino-5-(2-aminoethyl)-2(3H)-dihydrofuranone dihydrochloride as white crystals.

To a flask, 42 mg (0.19 mmol) of the resulting crude (3S,5R)-3-amino-5-(2-aminoethyl)-2(3H)-dihydrofuranone dihydrochloride, 0.56 ml (4.0 mmol) of triethylamine, and 1 ml of dichloromethane were fed, and 0.14 ml (1.0 mmol) of trifluoroacetic anhydride was added thereto under ice-cooling. The resulting reaction mixture was stirred for 2 hours and then concentrated, followed by purification by silica gel column chromatography. The resulting oily substance was dissolved in ethyl acetate, and then washed with an aqueous potassium carbonate solution and saturated brine. The aqueous layer was re-extracted with ethyl acetate, and the resulting organic layer was dried over magnesium sulfate, followed by concentrating the organic layer to obtain 43 mg of a brown oily substance. As a result of NMR analysis, this oily substance was found to be a mixture containing 34 wt % (3S,5R)-3-trifluoroacetylamino-5-(2-trifluoroacetylaminoethyl)-2(3H)-dihydrofuranone (0.044 mmol; yield, 23%) and 66 wt % triethylamine trifluoroacetate.

The results of NOESY measurement are shown in the following formula. Since cross peaks were found between the 3-position hydrogen atom (H3) and 5-position hydrogen atom (H5), and between one 4-position hydrogen atom (H4a) and the 3-position and 5-position hydrogen atoms, the substituents at the 3-position and the 5-position could be confirmed to have the cis configuration. Since the absolute configuration of the lysine used in the enzymatic reaction was S, it could be confirmed that the 3-trifluoroacetylamino-5-(2-trifluoroacetylaminoethyl)-2(3H)-dihydrofuranone has the stereochemistry of (3S,5R), and that the 4-hydroxylysine as its material has the stereochemistry of (2S,4R).

The results of measurement of physical properties of the resulting (3S,5R)-3-trifluoroacetylamino-5-(2-trifluoroacetylaminoethyl)-2(3H)-dihydrofuranone were as follows.

$^1$H-NMR (400 MHz, CDCl$_3$) δ 1.93-2.22 (3H, m, H$^{4b}$, H$^{1'}$×2), 2.76 (1H, ddd, J=12.6, 8.8, 5.6 Hz, H$^{4a}$), 3.51-3.56 (2H, m, H$^{2'}$), 4.52-4.60 (1H, m, H$^5$), 4.75 (1H, dd, J=11.9, 9.1 Hz, H3), 7.86 (1H, brs, NH), 8.87 (1H, brs, NH).

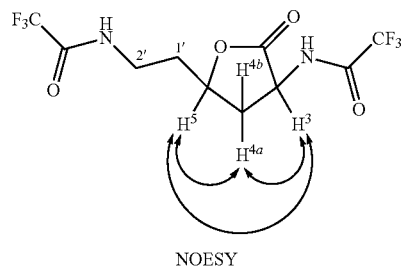

NOESY

Example 8

Production of (2S,4R)-4-Hydroxypipecolic Acid

In a plastic tube, 0.75 mL of 1 M tris hydroxymethyl aminomethane buffer (pH 8.0), 9.21 mL of desalted water, 86 mg of the (2S,4R)-4-hydroxylysine obtained in Example 6, 0.083 ml of 50 mM NADPH, 0.7 ml of 1.0 M glucose, and 1.25 ml of a 100-g/L suspension of the recombinant E. coli JM109/pKW32 (dpkA, aip, gdh, kr) obtained in Reference Example 1 were mixed together, and the reaction was allowed to proceed at 30° C. at pH 8.0 at a stirring rate of 1000 rpm for 20 hours. Completion of the reaction was judged by confirming disappearance of the peak for (2S, 4R)-4-hydroxylysine by HPLC analysis. From the liquid after the completion of the reaction, bacterial cells and bacterial debris were removed by centrifugation, to obtain 10.5 g of a supernatant.

The conditions for analyzing the (2S,4R)-4-hydroxylysine by HPLC were as follows.

Column, CLC-D (4.6 mm×150 mm), manufactured by SUPELCO; mobile phase, 2 mM copper sulfate; flow rate, 1.0 mL/minute; column temperature, 30° C.; and UV, 254 nm.

After passing 10.5 g of the supernatant through an ion-exchange resin column (DIAION (registered trademark) SK-1B (Type H), 4.0 g), washing was carried out with water, followed by elution with an aqueous solution containing 16.4 mmol ammonia. The ammonia eluate was concentrated to obtain 219 mg of a solid brown substance. As a result of NMR analysis, this solid substance was found to be a mixture containing 22 wt % (2S,4R)-4-hydroxypipecolic acid (0.33 mmol; yield, 62.6%) and 78 wt % tris hydroxymethyl aminomethane.

The results of measurement of physical properties of the resulting (2S,4R)-4-hydroxypipecolic acid were as follows.

$^1$H-NMR (400 MHz, $D_2O$) δ, 1.28-1.45 (2H, m), 1.91-1.99 (1H, m), 2.26-2.33 (1H, m), 2.77 (1H, td, J=13.2, 3.1 Hz), 3.25 (1H, ddd, J=13.2, 4.4, 2.6 Hz), 3.36-3.41 (1H, m), 3.78 (1H, tt, J=11.1, 4.5 Hz).

INDUSTRIAL APPLICABILITY

The present invention can be used as a method for producing hydroxy-L-lysine, which is useful as an intermediate for pharmaceuticals and the like, and can also be used as a method for producing hydroxy-L-pipecolic acid using the hydroxy-L-lysine obtained.

The invention claimed is:

1. A method for producing hydroxy-L-lysine, said method comprising reacting free L-lysine with 2-oxoglutarate-dependent L-lysine hydroxylase, an isolated cell comprising the 2-oxoglutarate-dependent L-lysine hydroxylase, a processed product of said cell, wherein the processed product comprises the 2-oxoglutarate-dependent L-lysine hydroxylase, and/or a culture broth comprising the 2-oxoglutarate-dependent L-lysine hydroxylase obtained by culturing said cell, in an aqueous medium, or a mixture of the aqueous medium and an organic solvent that contains the free L-lysine, to convert the free L-lysine to hydroxy-L-lysine represented by the following General Formula (I):

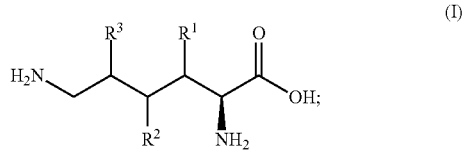

and
collecting the hydroxy-L-lysine,
wherein each of $R^1$, $R^2$ and $R^3$ represents a hydrogen atom or hydroxyl group, with the proviso that at least one of $R^1$, $R^2$ and $R^3$ represents a hydroxyl group; and
wherein said 2-oxoglutarate-dependent L-lysine hydroxylase comprises a polypeptide selected from the group consisting of:
(A) a polypeptide comprising the amino acid sequence of SEQ ID NO:2, 4, 6, 8, 10, or 12;
(B) a polypeptide comprising the amino acid sequence of SEQ ID NO:2, 4, 6, 8, 10, or 12 except that at least one and not more than 10 amino acids are deleted, substituted, and/or added, wherein the polypeptide has 2-oxoglutarate-dependent L-lysine hydroxylase activity; and
(C) a polypeptide comprising an amino acid sequence with a sequence identity of not less than 90% to the amino acid sequence of SEQ ID NO:2, 4, 6, 8, 10, or 12, wherein the polypeptide has 2-oxoglutarate-dependent L-lysine hydroxylase activity.

2. The method for producing hydroxy-L-lysine according to claim 1, wherein said 2-oxoglutarate-dependent L-lysine hydroxylase comprises a polypeptide selected from the group consisting of:
(A) a polypeptide comprising the amino acid sequence of SEQ ID NO:2, 6, 8, or 10;
(B) a polypeptide comprising the amino acid sequence of SEQ ID NO:2, 6, 8, or 10 except that at least one and not more than 10 amino acids are deleted, substituted, and/or added, wherein the polypeptide has 2-oxoglutarate-dependent L-lysine hydroxylase activity; and
(C) a polypeptide comprising an amino acid sequence with a sequence identity of not less than 90% to the amino acid sequence of SEQ ID NO:2, 6, 8, or 10, wherein the polypeptide has 2-oxoglutarate-dependent L-lysine hydroxylase activity.

3. The method for producing, hydroxy-L-lysine according to claim 1, wherein
the free L-lysine is reacted with the isolated cell comprising the 2-oxoglutarate-dependent L-lysine hydroxylase, the processed product of said cell comprising the 2-oxoglutarate-dependent L-lysine hydroxylase, and/or the culture broth comprising the 2-oxoglutarate-dependent L-lysine hydroxylase obtained by culturing said cell; and
said cell comprising the 2-oxoglutarate-dependent L-lysine hydroxylase is a cell transformed with a DNA encoding the 2-oxoglutarate-dependent L-lysine hydroxylase.

4. The method for producing hydroxy-L-lysine according, to claim 3, wherein said DNA encoding the 2-oxoglutarate-dependent L-lysine hydroxylase comprises a DNA selected from the group consisting of:
(A) a DNA comprising the nucleotide sequence of SEQ ID NO:1, 3, 5, 7, 9, or 11;
(B) a DNA comprising the nucleotide sequence of SEQ ID NO:1, 3, 5, 7, 9, or 11 except that at least one and not more than 30 nucleotides are substituted, deleted, and/or added, wherein the DNA encodes a polypeptide having 2-oxoglutarate-dependent L-lysine hydroxylase activity; and
(C) a DNA comprising a nucleotide sequence which hybridizes with the full complementary strand of the nucleotide sequence of SEQ ID NO:1, 3, 5, 7, 9, or 11 under stringent conditions comprising washing with 0.1×SSC and 0.1% SDS at 60° C., wherein the DNA encodes a polypeptide having 2-oxoglutarate-dependent hydroxylase activity.

5. The method for producing hydroxy-L-lysine according to claim 1, wherein the free L-lysine is reacted with said 2-oxoglutarate-dependent L-lysine hydroxylase, the isolated cell comprising the 2-oxoglutarate-dependent L-lysine hydroxylase, the processed product of said cell comprising the 2-oxoglutarate-dependent L-lysine hydroxylase, and/or the culture broth comprising the 2-oxoglutarate-dependent L-lysine hydroxylase obtained by culturing said cell in the presence of 2-oxoglutaric acid and ferrous ion.

6. A method for producing hydroxy-L-pipecolic acid, said method comprising:
producing, hydroxy-L-lysine by the method of claim 1;
reacting the collected hydroxy-L-lysine with: (i) at least one enzyme selected from the group consisting of L-amino acid oxidase, L-amino acid dehydrogenase, and L-amino acid transferase, or (ii) amino acid racemase and at least one enzyme selected from the group consisting of D-amino acid oxidase, D-amino acid dehydrogenase, and D-amino acid transferase, to produce a compound represented by the following General Formula (II):

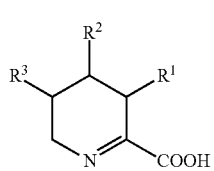
(II)

wherein $R^1$, $R^2$, and $R^3$ have the same meanings as in the General Formula (I) of claim 1; and
reacting the compound represented by the General Formula (II) with N-methyl-L-amino acid dehydrogenase to produce hydroxy-L-pipecolic acid represented by the following General Formula (III):

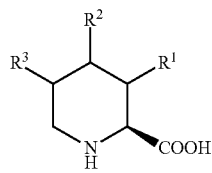
(III)

wherein $R^1$, $R^2$, and $R^3$ have the same meanings as in the General Formula (I) of claim 1.

7. A method for producing hydroxy-L-pipecolic acid, said method comprising:
producing hydroxy-L-lysine by the method of claim 1;
reacting the collected hydroxy-L-lysine with at least one enzyme selected from the group consisting of L-lysine 6-oxidase, 6-dehydrogenase, and L-lysine 6-transferase, to produce a compound represented by the following General Formula (IV):

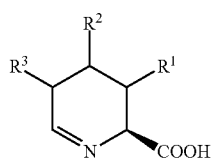
(IV)

wherein $R^1$, $R^2$, and $R^3$ have the same meanings as in the General Formula (I) of claim 1; and
reacting the compound represented by the General Formula (IV) with pyrroline-5-carboxylate reductase to produce hydroxy-L-pipecolic acid represented by the following General Formula (III):

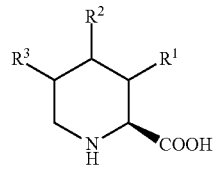
(III)

wherein $R^1$, $R^2$, and $R^3$ have the same meanings as in the General Formula (I) of claim 1.

8. A method for producing hydroxy-L-pipecolic acid, said method comprising:
producing hydroxy-L-lysine by the method of claim 1; and
reacting the collected hydroxy-L-lysine with lysine cyclodeaminase to produce hydroxy-L-pipecolic acid represented by the following General Formula (III):

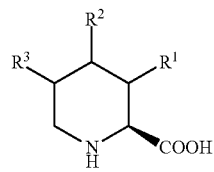
(III)

wherein $R^1$, $R^2$, and $R^3$ have the same meanings as in the General Formula (I) of claim 1.

9. The method for producing hydroxy-L-lysine according to claim 1, wherein said 2-oxoglutarate-dependent L-lysine hydroxylase comprises a polypeptide selected from the group consisting of:
(A) a polypeptide comprising the amino acid sequence of SEQ ID NO:4 or 12;
(B) a polypeptide comprising the amino acid sequence of SEQ ID NO:4 or 12 except that at least one and not more than 10 amino acids are deleted substituted, and/or added, wherein the polypeptide has 2-oxoglutarate-dependent L-lysine hydroxylase activity; and
(C) a polypeptide comprising an amino acid sequence with a sequence identity of not less than 90% to the amino acid sequence of SEQ ID NO:4 or 12, wherein the polypeptide has 2-oxoglutarate-dependent L-lysine hydroxylase activity.

* * * * *

UNITED STATES PATENT AND TRADEMARK OFFICE
CERTIFICATE OF CORRECTION

PATENT NO.        : 9,512,452 B2                                Page 1 of 1
APPLICATION NO.   : 14/431193
DATED             : December 6, 2016
INVENTOR(S)       : Kuniki Kino et al.

It is certified that error appears in the above-identified patent and that said Letters Patent is hereby corrected as shown below:

On the Title Page

At item (57), Line 13, " 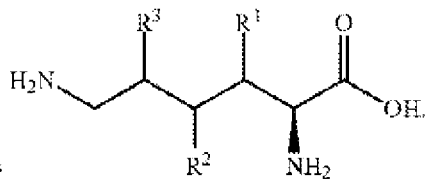 " should be

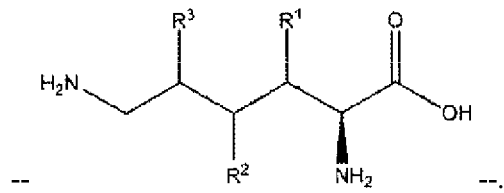

-- --.

In the Claims

At Column 80, Line 25, "producing," should be -- producing --.

At Column 80, Line 39, "according," should be -- according --.

At Column 80, Line 57, "hydroxylase" should be -- L-lysine hydroxylase --.

At Column 81, Line 3, "producing," should be -- producing --.

At Column 81, Line 45, "6-dehydrogenase," should be -- L-lysine 6-dehydrogenase, --.

At Column 82, Line 48, "deleted" should be -- deleted, --.

Signed and Sealed this
Second Day of May, 2017

Michelle K. Lee
*Director of the United States Patent and Trademark Office*

SEQUENCE LISTING

```
<160> NUMBER OF SEQ ID NOS: 38

<210> SEQ ID NO 1
<211> LENGTH: 1113
<212> TYPE: DNA
<213> ORGANISM: Flavobacterium johnsoniae NBRC14942
<220> FEATURE:
<221> NAME/KEY: CDS
<222> LOCATION: (1)..(1110)

<400> SEQUENCE: 1 atg aaa tca caa tca tta att gaa gat gag ata cca gta aaa gaa aac        48
Met Lys Ser Gln Ser Leu Ile Glu Asp Glu Ile Pro Val Lys Glu Asn
1               5                   10                  15 tat gct tat caa att cct aca agc ccg ctg ata gtg gag gtt acg cct        96
Tyr Ala Tyr Gln Ile Pro Thr Ser Pro Leu Ile Val Glu Val Thr Pro
                20                  25                  30 cag gaa aga aac att ttg tct aat gtg ggc gct ctg ctg gaa aag gca       144
Gln Glu Arg Asn Ile Leu Ser Asn Val Gly Ala Leu Leu Glu Lys Ala
            35                  40                  45 ttt aag agc tat gaa aac cca gat tat ata gaa gcg ctt cat ctg tat       192
Phe Lys Ser Tyr Glu Asn Pro Asp Tyr Ile Glu Ala Leu His Leu Tyr
        50                  55                  60 tct ttt cag ctt ctt cca gaa aga ata gcc aga att tta agc cgt ttt       240
Ser Phe Gln Leu Leu Pro Glu Arg Ile Ala Arg Ile Leu Ser Arg Phe
65                  70                  75                  80 gga aca gat ttc tca gct gat cag tat ggc gct att att ttt aga ggt       288
Gly Thr Asp Phe Ser Ala Asp Gln Tyr Gly Ala Ile Ile Phe Arg Gly
                85                  90                  95 ctt ctt gaa gtt gat cag gat cat ctg gga cca act cct gcg aat tgg       336
Leu Leu Glu Val Asp Gln Asp His Leu Gly Pro Thr Pro Ala Asn Trp
                100                 105                 110 cag agc gct gat tac tca aaa ctc aat aaa tac ggc ttt att tgt tcc       384
Gln Ser Ala Asp Tyr Ser Lys Leu Asn Lys Tyr Gly Phe Ile Cys Ser
            115                 120                 125 ttg ctg cat ggt gca gtt cct tca aaa cca gta caa tat tat gcg cag       432
Leu Leu His Gly Ala Val Pro Ser Lys Pro Val Gln Tyr Tyr Ala Gln
        130                 135                 140 aga aag ggc ggg gga att ctt cat gct gtt att cca gat gag aaa atg       480
Arg Lys Gly Gly Gly Ile Leu His Ala Val Ile Pro Asp Glu Lys Met
145                 150                 155                 160 gca gct acg caa aca ggt tcg gga tca aaa aca aat ttg tat gtt cat       528
Ala Ala Thr Gln Thr Gly Ser Gly Ser Lys Thr Asn Leu Tyr Val His
                165                 170                 175 aca gaa gat gct ttt ctt tta cat cag gct gat ttt tta agt ttt cta       576
Thr Glu Asp Ala Phe Leu Leu His Gln Ala Asp Phe Leu Ser Phe Leu
                180                 185                 190 tat ctg cga aat gaa gaa aga gtt cct tct aca ctt tac tca gta agg       624
Tyr Leu Arg Asn Glu Glu Arg Val Pro Ser Thr Leu Tyr Ser Val Arg
```

```
                195                 200                 205
tcg cat ggt aag gtg aat aag ata atg gaa aag ctt ttt gat cca att      672
Ser His Gly Lys Val Asn Lys Ile Met Glu Lys Leu Phe Asp Pro Ile
    210                 215                 220 tat caa tgt cct aaa gat gct aat tat cag gaa gaa att aat gat ggt      720
Tyr Gln Cys Pro Lys Asp Ala Asn Tyr Gln Glu Glu Ile Asn Asp Gly
225                 230                 235                 240 ccg ctg gct tct gtt tta tat gga aat aaa aag ctg cct ttt att aga      768
Pro Leu Ala Ser Val Leu Tyr Gly Asn Lys Lys Leu Pro Phe Ile Arg
                245                 250                 255 ttt gat gca gca gag cag ata ttt aat gaa aac gcc gga cag act ccc      816
Phe Asp Ala Ala Glu Gln Ile Phe Asn Glu Asn Ala Gly Gln Thr Pro
            260                 265                 270 gaa gct ctt tac aat tta act gaa ttt tgg aat gaa gct aaa gag ttg      864
Glu Ala Leu Tyr Asn Leu Thr Glu Phe Trp Asn Glu Ala Lys Glu Leu
        275                 280                 285 att aat agt gat tat atc cca gat tct ggt gat gtt ata ttt gta aat      912
Ile Asn Ser Asp Tyr Ile Pro Asp Ser Gly Asp Val Ile Phe Val Asn
    290                 295                 300 aat cat ttg tgt gct cac gga aga agt gct ttt aca gca ggg cag aaa      960
Asn His Leu Cys Ala His Gly Arg Ser Ala Phe Thr Ala Gly Gln Lys
305                 310                 315                 320 gag gag aat ggt aag ctt gtg cca tgt gag aga cga caa atg tta aga     1008
Glu Glu Asn Gly Lys Leu Val Pro Cys Glu Arg Arg Gln Met Leu Arg
                325                 330                 335 atg atg agc aaa acc agt cta att cat ata aga tca atg aca cat acc     1056
Met Met Ser Lys Thr Ser Leu Ile His Ile Arg Ser Met Thr His Thr
            340                 345                 350 gat gat ccg tat ttt gtt atg gaa gaa cat tta gga aaa gtt ttt gat     1104
Asp Asp Pro Tyr Phe Val Met Glu Glu His Leu Gly Lys Val Phe Asp
        355                 360                 365 cag gct taa                                                         1113
Gln Ala
    370

<210> SEQ ID NO 2
<211> LENGTH: 370
<212> TYPE: PRT
<213> ORGANISM: Flavobacterium johnsoniae NBRC14942

<400> SEQUENCE: 2

Met Lys Ser Gln Ser Leu Ile Glu Asp Glu Ile Pro Val Lys Glu Asn
1               5                   10                  15

Tyr Ala Tyr Gln Ile Pro Thr Ser Pro Leu Ile Val Glu Val Thr Pro
            20                  25                  30

Gln Glu Arg Asn Ile Leu Ser Asn Val Gly Ala Leu Leu Glu Lys Ala
        35                  40                  45

Phe Lys Ser Tyr Glu Asn Pro Asp Tyr Ile Glu Ala Leu His Leu Tyr
    50                  55                  60

Ser Phe Gln Leu Leu Pro Glu Arg Ile Ala Arg Ile Leu Ser Arg Phe
65                  70                  75                  80

Gly Thr Asp Phe Ser Ala Asp Gln Tyr Gly Ala Ile Ile Phe Arg Gly
            85                  90                  95

Leu Leu Glu Val Asp Gln Asp His Leu Gly Pro Thr Pro Ala Asn Trp
        100                 105                 110

Gln Ser Ala Asp Tyr Ser Lys Leu Asn Lys Tyr Gly Phe Ile Cys Ser
    115                 120                 125

Leu Leu His Gly Ala Val Pro Ser Lys Pro Val Gln Tyr Tyr Ala Gln
```

-continued

```
                130                 135                 140
Arg Lys Gly Gly Gly Ile Leu His Ala Val Ile Pro Asp Glu Lys Met
145                 150                 155                 160

Ala Ala Thr Gln Thr Gly Ser Gly Ser Lys Thr Asn Leu Tyr Val His
                165                 170                 175

Thr Glu Asp Ala Phe Leu Leu His Gln Ala Asp Phe Leu Ser Phe Leu
            180                 185                 190

Tyr Leu Arg Asn Glu Glu Arg Val Pro Ser Thr Leu Tyr Ser Val Arg
        195                 200                 205

Ser His Gly Lys Val Asn Lys Ile Met Glu Lys Leu Phe Asp Pro Ile
    210                 215                 220

Tyr Gln Cys Pro Lys Asp Ala Asn Tyr Gln Glu Ile Asn Asp Gly
225                 230                 235                 240

Pro Leu Ala Ser Val Leu Tyr Gly Asn Lys Lys Leu Pro Phe Ile Arg
                245                 250                 255

Phe Asp Ala Ala Glu Gln Ile Phe Asn Glu Asn Ala Gly Gln Thr Pro
            260                 265                 270

Glu Ala Leu Tyr Asn Leu Thr Glu Phe Trp Asn Glu Ala Lys Glu Leu
        275                 280                 285

Ile Asn Ser Asp Tyr Ile Pro Asp Ser Gly Asp Val Ile Phe Val Asn
    290                 295                 300

Asn His Leu Cys Ala His Gly Arg Ser Ala Phe Thr Ala Gly Gln Lys
305                 310                 315                 320

Glu Glu Asn Gly Lys Leu Val Pro Cys Glu Arg Arg Gln Met Leu Arg
                325                 330                 335

Met Met Ser Lys Thr Ser Leu Ile His Ile Arg Ser Met Thr His Thr
            340                 345                 350

Asp Asp Pro Tyr Phe Val Met Glu Glu His Leu Gly Lys Val Phe Asp
        355                 360                 365

Gln Ala
    370

<210> SEQ ID NO 3
<211> LENGTH: 996
<212> TYPE: DNA
<213> ORGANISM: Kineococcus radiotolerans NBRC101839
<220> FEATURE:
<221> NAME/KEY: CDS
<222> LOCATION: (1)..(993)

<400> SEQUENCE: 3 gtg tcc tcg ctg ttc ctc gac tcc tcc gcc cac gtg ccg acc ctg ttc      48
Val Ser Ser Leu Phe Leu Asp Ser Ser Ala His Val Pro Thr Leu Phe
1               5                   10                  15 gag ctg ccc gcg ccc cag cgg gcc gcg ctg gcg gcg ctg ggc gcg cgc      96
Glu Leu Pro Ala Pro Gln Arg Ala Ala Leu Ala Ala Leu Gly Ala Arg
                20                  25                  30 ctg acc gcg gac ccg gtg acc gag ccc gac gcc ttc ggc cgc cag gcg     144
Leu Thr Ala Asp Pro Val Thr Glu Pro Asp Ala Phe Gly Arg Gln Ala
            35                  40                  45 cgc ctg ctg gcc cgc gaa ctg tcc gtc gag gtc acc gag gcc ctg tgg     192
Arg Leu Leu Ala Arg Glu Leu Ser Val Glu Val Thr Glu Ala Leu Trp
        50                  55                  60 gcg ttc gag gaa cgg gga tcg gac tcc ggg gtc ctc gtc ctg cgc ggc     240
Ala Phe Glu Glu Arg Gly Ser Asp Ser Gly Val Leu Val Leu Arg Gly
65                  70                  75                  80 ctg gag gtc ggt gag ctg ccg ccc acc ccg gcc gac aac acc ggc ggg     288
```

-continued

```
                Leu Glu Val Gly Glu Leu Pro Pro Thr Pro Ala Asp Asn Thr Gly Gly
                                 85                  90                  95 atc ggc ggg cgc acc ctg ctc gcc cgc cag cag gcg atc gtc agc cac        336
Ile Gly Gly Arg Thr Leu Leu Ala Arg Gln Gln Ala Ile Val Ser His
            100                 105                 110 gcg ctg ggg cac atg gtc ggc tac gcc gcc gag ggc cac ggg cac ctc        384
Ala Leu Gly His Met Val Gly Tyr Ala Ala Glu Gly His Gly His Leu
        115                 120                 125 ctg cag gac atg gtc ccc aac gcc agg ctc gcc gcg acc cag cag tcg        432
Leu Gln Asp Met Val Pro Asn Ala Arg Leu Ala Ala Thr Gln Gln Ser
    130                 135                 140 cag ggc tcc cgg gtg gag ctg gag gcg cac acc gag cag tgc ttc tcc        480
Gln Gly Ser Arg Val Glu Leu Glu Ala His Thr Glu Gln Cys Phe Ser
145                 150                 155                 160 gac ctg cgc ccc gac tac gtc gtc ctg ggc tgc ctg cgc ggg gac gcc        528
Asp Leu Arg Pro Asp Tyr Val Val Leu Gly Cys Leu Arg Gly Asp Ala
                165                 170                 175 gac gcc gcc acc tac gcg ttc cgc gcc ctg gac ctg ctg gcc cac gtg        576
Asp Ala Ala Thr Tyr Ala Phe Arg Ala Leu Asp Leu Leu Ala His Val
            180                 185                 190 gac ccc acc gac gtc atg gag ctg ttc cgg ccg ctg tgg acg acg ctg        624
Asp Pro Thr Asp Val Met Glu Leu Phe Arg Pro Leu Trp Thr Thr Leu
        195                 200                 205 gtc gac gag tcc ttc gcc gac ttc ctc gac acc cgc gag gtg cgc ggg        672
Val Asp Glu Ser Phe Ala Asp Phe Leu Asp Thr Arg Glu Val Arg Gly
    210                 215                 220 ccg ttc tcc atc ctc tcc ggc gac gtc gac gac ccg acg atg ctc gtc        720
Pro Phe Ser Ile Leu Ser Gly Asp Val Asp Asp Pro Thr Met Leu Val
225                 230                 235                 240 gac cag gac ctc atg cac ggc atc acc aag cac gcc cag gcc ctg ctg        768
Asp Gln Asp Leu Met His Gly Ile Thr Lys His Ala Gln Ala Leu Leu
                245                 250                 255 gag cgc gtg ctg gag atc tac gtc gcc cac cgc cac gcc gtc gtc ctc        816
Glu Arg Val Leu Glu Ile Tyr Val Ala His Arg His Ala Val Val Leu
            260                 265                 270 cag ccc ggg gac gtg ctg ctg ctg gac aac ctg cgc gcc atg cac ggc        864
Gln Pro Gly Asp Val Leu Leu Leu Asp Asn Leu Arg Ala Met His Gly
        275                 280                 285 cgc tcg ccg ttc gcc ccg cgc ttc gac ggc acc gac cgg ttc atc tcc        912
Arg Ser Pro Phe Ala Pro Arg Phe Asp Gly Thr Asp Arg Phe Ile Ser
    290                 295                 300 cgg ggt ttc gtc gtc cgc gac ctg cgc cgc tcc cgc ttc gcc cgc ccc        960
Arg Gly Phe Val Val Arg Asp Leu Arg Arg Ser Arg Phe Ala Arg Pro
305                 310                 315                 320 ggc ggg aac cgc gtc gtg cag gcc agc ttc agc tga                        996
Gly Gly Asn Arg Val Val Gln Ala Ser Phe Ser
                325                 330

<210> SEQ ID NO 4
<211> LENGTH: 331
<212> TYPE: PRT
<213> ORGANISM: Kineococcus radiotolerans NBRC101839

<400> SEQUENCE: 4

Val Ser Ser Leu Phe Leu Asp Ser Ala His Val Pro Thr Leu Phe
1               5                   10                  15

Glu Leu Pro Ala Pro Gln Arg Ala Ala Leu Ala Ala Leu Gly Ala Arg
            20                  25                  30

Leu Thr Ala Asp Pro Val Thr Glu Pro Asp Ala Phe Gly Arg Gln Ala
        35                  40                  45
```

```
Arg Leu Leu Ala Arg Glu Leu Ser Val Glu Val Thr Glu Ala Leu Trp
             50                  55                  60

Ala Phe Glu Glu Arg Gly Ser Asp Ser Gly Val Leu Val Leu Arg Gly
 65                  70                  75                  80

Leu Glu Val Gly Glu Leu Pro Pro Thr Pro Ala Asp Asn Thr Gly Gly
                 85                  90                  95

Ile Gly Gly Arg Thr Leu Leu Ala Arg Gln Gln Ala Ile Val Ser His
                100                 105                 110

Ala Leu Gly His Met Val Gly Tyr Ala Ala Glu Gly His Gly His Leu
            115                 120                 125

Leu Gln Asp Met Val Pro Asn Ala Arg Leu Ala Ala Thr Gln Gln Ser
        130                 135                 140

Gln Gly Ser Arg Val Glu Leu Glu Ala His Thr Glu Gln Cys Phe Ser
145                 150                 155                 160

Asp Leu Arg Pro Asp Tyr Val Val Leu Gly Cys Leu Arg Gly Asp Ala
                165                 170                 175

Asp Ala Ala Thr Tyr Ala Phe Arg Ala Leu Asp Leu Leu Ala His Val
            180                 185                 190

Asp Pro Thr Asp Val Met Glu Leu Phe Arg Pro Leu Trp Thr Thr Leu
        195                 200                 205

Val Asp Glu Ser Phe Ala Asp Phe Leu Asp Thr Arg Glu Val Arg Gly
210                 215                 220

Pro Phe Ser Ile Leu Ser Gly Asp Val Asp Asp Pro Thr Met Leu Val
225                 230                 235                 240

Asp Gln Asp Leu Met His Gly Ile Thr Lys His Ala Gln Ala Leu Leu
                245                 250                 255

Glu Arg Val Leu Glu Ile Tyr Val Ala His Arg His Ala Val Val Leu
            260                 265                 270

Gln Pro Gly Asp Val Leu Leu Leu Asp Asn Leu Arg Ala Met His Gly
        275                 280                 285

Arg Ser Pro Phe Ala Pro Arg Phe Asp Gly Thr Asp Arg Phe Ile Ser
290                 295                 300

Arg Gly Phe Val Val Arg Asp Leu Arg Arg Ser Arg Phe Ala Arg Pro
305                 310                 315                 320

Gly Gly Asn Arg Val Val Gln Ala Ser Phe Ser
                325                 330

<210> SEQ ID NO 5
<211> LENGTH: 1149
<212> TYPE: DNA
<213> ORGANISM: Chitinophaga pinensis NBRC15968
<220> FEATURE:
<221> NAME/KEY: CDS
<222> LOCATION: (1)..(1146)

<400> SEQUENCE: 5 atg aga ccc tta gac gtg aca ccc aca att agc cca gga gcc cag gac     48
Met Arg Pro Leu Asp Val Thr Pro Thr Ile Ser Pro Gly Ala Gln Asp
 1               5                  10                  15 ctt ccg cgc act atg cat ttt gct gct gaa cct cct tta cag cct ttg     96
Leu Pro Arg Thr Met His Phe Ala Ala Glu Pro Pro Leu Gln Pro Leu
             20                  25                  30 ata ata gat att act gaa gaa gaa aaa ctg gaa att acc tat atc ggg    144
Ile Ile Asp Ile Thr Glu Glu Glu Lys Leu Glu Ile Thr Tyr Ile Gly
         35                  40                  45 aaa aag cta aaa aga aag tat aaa agc tat gat gat ccc ggt ttt att    192
```

```
                Lys Lys Leu Lys Arg Lys Tyr Lys Ser Tyr Asp Asp Pro Gly Phe Ile
                    50                  55                  60 tca atg ctg cac tta aat gcc tat acg ctg cta ccg gag cgt ata gca        240
Ser Met Leu His Leu Asn Ala Tyr Thr Leu Leu Pro Glu Arg Ile Ala
 65                  70                  75                  80 aag gtg ctg agt aat ttc ggt aca gac ttt tcc gac cag caa tac gga        288
Lys Val Leu Ser Asn Phe Gly Thr Asp Phe Ser Asp Gln Gln Tyr Gly
                     85                  90                  95 gct gtc gta ttg cgt gga ctg ata gaa ata ggt cag gat gaa tta ggc        336
Ala Val Val Leu Arg Gly Leu Ile Glu Ile Gly Gln Asp Glu Leu Gly
                    100                 105                 110 cca acc cca cgt tcc tgg cag gaa acc gac cat gaa aag att atg gaa        384
Pro Thr Pro Arg Ser Trp Gln Glu Thr Asp His Glu Lys Ile Met Glu
                115                 120                 125 tat ggc ttc att tcc tcc tta tta cat ggc gct gta cca tcc aaa ccc        432
Tyr Gly Phe Ile Ser Ser Leu Leu His Gly Ala Val Pro Ser Lys Pro
            130                 135                 140 gtc gag tat ttc gcg cag cga aaa ggt ggt ggc tta atg cac gcg att        480
Val Glu Tyr Phe Ala Gln Arg Lys Gly Gly Gly Leu Met His Ala Ile
145                 150                 155                 160 att cct gat gag aat atg agc ttt aca caa aca ggc tca ggt tcc cgt        528
Ile Pro Asp Glu Asn Met Ser Phe Thr Gln Thr Gly Ser Gly Ser Arg
                165                 170                 175 aca gat ctt ttt gta cat aca gaa gat gct ttc ctg cat aat gcg gct        576
Thr Asp Leu Phe Val His Thr Glu Asp Ala Phe Leu His Asn Ala Ala
                180                 185                 190 gat ttt ctg agt ttt ctt ttc ctg cgg aat gaa gaa cgt gtg cct tcc        624
Asp Phe Leu Ser Phe Leu Phe Leu Arg Asn Glu Glu Arg Val Pro Ser
            195                 200                 205 acc tta tat tct atc cgc tct cat ggc aga ccg gat gcg ata tta cag        672
Thr Leu Tyr Ser Ile Arg Ser His Gly Arg Pro Asp Ala Ile Leu Gln
210                 215                 220 gag ctt ttc aag cct atc tat aag tgt ccg aag gat gcg aac tat gct        720
Glu Leu Phe Lys Pro Ile Tyr Lys Cys Pro Lys Asp Ala Asn Tyr Ala
225                 230                 235                 240 tcc gaa gaa gcc ctg gga gat gac atc cgt act tct gtt tta tat ggt        768
Ser Glu Glu Ala Leu Gly Asp Asp Ile Arg Thr Ser Val Leu Tyr Gly
                245                 250                 255 agc aga tcc gct ccc ttc atg cgc ttt gat gct gcg gaa cag att tat        816
Ser Arg Ser Ala Pro Phe Met Arg Phe Asp Ala Ala Glu Gln Ile Tyr
                260                 265                 270 aat gaa gac gcc aat cag gat cct gaa gct tta cat aat ctg aaa aga        864
Asn Glu Asp Ala Asn Gln Asp Pro Glu Ala Leu His Asn Leu Lys Arg
            275                 280                 285 ttc tgg gaa gag gcg cgc aaa ctg ata tat aat gac ttc gtt cct gag        912
Phe Trp Glu Glu Ala Arg Lys Leu Ile Tyr Asn Asp Phe Val Pro Glu
290                 295                 300 tca ggt gac ctg atc ttt gtg aat aat cat ctt tgt gcc cat ggc cgg        960
Ser Gly Asp Leu Ile Phe Val Asn Asn His Leu Cys Ala His Gly Arg
305                 310                 315                 320 aat gct ttc ctg gca ggc ttc aga gag gaa aat ggt cag ctg gta aaa       1008
Asn Ala Phe Leu Ala Gly Phe Arg Glu Glu Asn Gly Gln Leu Val Lys
                325                 330                 335 tgc gaa cgc cgt ctt atg tta cgt atg atg agc aaa acc agc ctg att       1056
Cys Glu Arg Arg Leu Met Leu Arg Met Met Ser Lys Thr Ser Leu Ile
                340                 345                 350 aac atc cgt gaa gta acc cac ccc gaa aac cct tat ctc atc atg gaa       1104
Asn Ile Arg Glu Val Thr His Pro Glu Asn Pro Tyr Leu Ile Met Glu
            355                 360                 365
```

```
gag cac tac gga aaa gta tat agc gct cac ctg gca aac ctt taa         1149
Glu His Tyr Gly Lys Val Tyr Ser Ala His Leu Ala Asn Leu
370             375                 380
```

<210> SEQ ID NO 6
<211> LENGTH: 382
<212> TYPE: PRT
<213> ORGANISM: Chitinophaga pinensis NBRC15968

<400> SEQUENCE: 6

```
Met Arg Pro Leu Asp Val Thr Pro Thr Ile Ser Pro Gly Ala Gln Asp
1               5                   10                  15

Leu Pro Arg Thr Met His Phe Ala Ala Glu Pro Pro Leu Gln Pro Leu
            20                  25                  30

Ile Ile Asp Ile Thr Glu Glu Lys Leu Glu Ile Thr Tyr Ile Gly
        35                  40                  45

Lys Lys Leu Lys Arg Lys Tyr Lys Ser Tyr Asp Asp Pro Gly Phe Ile
    50                  55                  60

Ser Met Leu His Leu Asn Ala Tyr Thr Leu Leu Pro Glu Arg Ile Ala
65                  70                  75                  80

Lys Val Leu Ser Asn Phe Gly Thr Asp Phe Ser Asp Gln Gln Tyr Gly
                85                  90                  95

Ala Val Val Leu Arg Gly Leu Ile Glu Ile Gly Gln Asp Glu Leu Gly
            100                 105                 110

Pro Thr Pro Arg Ser Trp Gln Glu Thr Asp His Glu Lys Ile Met Glu
        115                 120                 125

Tyr Gly Phe Ile Ser Ser Leu Leu His Gly Ala Val Pro Ser Lys Pro
    130                 135                 140

Val Glu Tyr Phe Ala Gln Arg Lys Gly Gly Gly Leu Met His Ala Ile
145                 150                 155                 160

Ile Pro Asp Glu Asn Met Ser Phe Thr Gln Thr Gly Ser Gly Ser Arg
                165                 170                 175

Thr Asp Leu Phe Val His Thr Glu Asp Ala Phe Leu His Asn Ala Ala
            180                 185                 190

Asp Phe Leu Ser Phe Leu Phe Leu Arg Asn Glu Glu Arg Val Pro Ser
        195                 200                 205

Thr Leu Tyr Ser Ile Arg Ser His Gly Arg Pro Asp Ala Ile Leu Gln
    210                 215                 220

Glu Leu Phe Lys Pro Ile Tyr Lys Cys Pro Lys Asp Ala Asn Tyr Ala
225                 230                 235                 240

Ser Glu Glu Ala Leu Gly Asp Asp Ile Arg Thr Ser Val Leu Tyr Gly
                245                 250                 255

Ser Arg Ser Ala Pro Phe Met Arg Phe Asp Ala Ala Glu Gln Ile Tyr
            260                 265                 270

Asn Glu Asp Ala Asn Gln Asp Pro Glu Ala Leu His Asn Leu Lys Arg
        275                 280                 285

Phe Trp Glu Glu Ala Arg Lys Leu Ile Tyr Asn Asp Phe Val Pro Glu
    290                 295                 300

Ser Gly Asp Leu Ile Phe Val Asn Asn His Leu Cys Ala His Gly Arg
305                 310                 315                 320

Asn Ala Phe Leu Ala Gly Phe Arg Glu Glu Asn Gly Gln Leu Val Lys
                325                 330                 335

Cys Glu Arg Arg Leu Met Leu Arg Met Met Ser Lys Thr Ser Leu Ile
            340                 345                 350

Asn Ile Arg Glu Val Thr His Pro Glu Asn Pro Tyr Leu Ile Met Glu
```

```
                355                 360                 365
        Glu His Tyr Gly Lys Val Tyr Ser Ala His Leu Ala Asn Leu
                370                 375                 380

<210> SEQ ID NO 7
<211> LENGTH: 1098
<212> TYPE: DNA
<213> ORGANISM: Chryseobacterium gleum NBRC15054
<220> FEATURE:
<221> NAME/KEY: CDS
<222> LOCATION: (1)..(1095)

<400> SEQUENCE: 7 atg aat tct aca caa att tta gat aaa gac tgt tta aca gca gta aag      48
Met Asn Ser Thr Gln Ile Leu Asp Lys Asp Cys Leu Thr Ala Val Lys
1               5                  10                  15 ctg ctt cct acg gtc ata gaa gtc act tct cag gag aga aga atg ata      96
Leu Leu Pro Thr Val Ile Glu Val Thr Ser Gln Glu Arg Arg Met Ile
                20                  25                  30 aaa gat gca gcg ctg cat ctt cag aaa aaa tat ggc act tat gaa aac     144
Lys Asp Ala Ala Leu His Leu Gln Lys Lys Tyr Gly Thr Tyr Glu Asn
            35                  40                  45 cgg gat ttt ata aaa cat gtt cat caa ctg gcc tct tat ttt ctt ccg     192
Arg Asp Phe Ile Lys His Val His Gln Leu Ala Ser Tyr Phe Leu Pro
        50                  55                  60 gaa agg att cta aat ata gca gct gat ttt gca agt gac ttt tct gaa     240
Glu Arg Ile Leu Asn Ile Ala Ala Asp Phe Ala Ser Asp Phe Ser Glu
65                  70                  75                  80 aat cag tat gga gcg ctg gtt ttt aca gga ttg atg gag ata gac cag     288
Asn Gln Tyr Gly Ala Leu Val Phe Thr Gly Leu Met Glu Ile Asp Gln
                85                  90                  95 gaa gaa ata ggt tct act cca ccc aac tgg caa tcg gca gat tat tca     336
Glu Glu Ile Gly Ser Thr Pro Pro Asn Trp Gln Ser Ala Asp Tyr Ser
                100                 105                 110 aag ttt aat tta tat ggt ttt gcg tgt gcg ctt att cat ggg gca ctt     384
Lys Phe Asn Leu Tyr Gly Phe Ala Cys Ala Leu Ile His Gly Ala Leu
            115                 120                 125 ccc tca aag cct gta caa tat tat tca cag cgt aaa ggc ggt gga ttg     432
Pro Ser Lys Pro Val Gln Tyr Tyr Ser Gln Arg Lys Gly Gly Gly Leu
        130                 135                 140 atc cac gct att att cct gat gaa aaa atg aaa gaa aca cag aca gga     480
Ile His Ala Ile Ile Pro Asp Glu Lys Met Lys Glu Thr Gln Thr Gly
145                 150                 155                 160 tca gga tcc tca acg gat ctg tat gta cat aca gaa gat gct ttt ctg     528
Ser Gly Ser Ser Thr Asp Leu Tyr Val His Thr Glu Asp Ala Phe Leu
                165                 170                 175 aaa cat cag gct gac ttt tta agc ttt atg tat gtc cga aat gaa gag     576
Lys His Gln Ala Asp Phe Leu Ser Phe Met Tyr Val Arg Asn Glu Glu
            180                 185                 190 cag gta cct tca act ctt tat tct atc cgt tct cat gag tct att ggg     624
Gln Val Pro Ser Thr Leu Tyr Ser Ile Arg Ser His Glu Ser Ile Gly
        195                 200                 205 gaa aag tac agg aca ctt ttt gag cct att tat aaa atc cct aaa gat     672
Glu Lys Tyr Arg Thr Leu Phe Glu Pro Ile Tyr Lys Ile Pro Lys Asp
    210                 215                 220 gcc aat ctg gaa acg gga gaa aat gaa gaa gaa act ctg gat tct gta     720
Ala Asn Leu Glu Thr Gly Glu Asn Glu Glu Glu Thr Leu Asp Ser Val
225                 230                 235                 240 ttg tat gga aat acc aac ctt cct ttt atg cga ttt gat gcg gcg gaa     768
Leu Tyr Gly Asn Thr Asn Leu Pro Phe Met Arg Phe Asp Ala Ala Glu
                245                 250                 255
```

```
cag ctt ttc aat tcc agt atc aga cag tca gaa gaa gcg cag cat aca      816
Gln Leu Phe Asn Ser Ser Ile Arg Gln Ser Glu Glu Ala Gln His Thr
            260                 265                 270 ctg cat gag ttc tgg gaa gaa gcc aga cat ttg att tat tca gga ttt      864
Leu His Glu Phe Trp Glu Glu Ala Arg His Leu Ile Tyr Ser Gly Phe
    275                 280                 285 acg cct cag gcc gga gat gtt att ctg gtt aat aat cat tta tgt gct      912
Thr Pro Gln Ala Gly Asp Val Ile Leu Val Asn Asn His Leu Cys Ala
290                 295                 300 cac gga aga tct gct ttc cgt gcg gga gta aga aat att gac ggt ata      960
His Gly Arg Ser Ala Phe Arg Ala Gly Val Arg Asn Ile Asp Gly Ile
305                 310                 315                 320 gaa cag ccg tgc gaa cga aga att atg ctt cgg atg atg agt aaa gtg     1008
Glu Gln Pro Cys Glu Arg Arg Ile Met Leu Arg Met Met Ser Lys Val
                325                 330                 335 agc ctt att gat atg aga gca cat acc ctt aca gaa gat cct ttt ttt     1056
Ser Leu Ile Asp Met Arg Ala His Thr Leu Thr Glu Asp Pro Phe Phe
            340                 345                 350 gtc ata gaa gaa cat ctg ggt aaa aac ttt caa cat ttt taa             1098
Val Ile Glu Glu His Leu Gly Lys Asn Phe Gln His Phe
    355                 360                 365

<210> SEQ ID NO 8
<211> LENGTH: 365
<212> TYPE: PRT
<213> ORGANISM: Chryseobacterium gleum NBRC15054

<400> SEQUENCE: 8

Met Asn Ser Thr Gln Ile Leu Asp Lys Asp Cys Leu Thr Ala Val Lys
1               5                   10                  15

Leu Leu Pro Thr Val Ile Glu Val Thr Ser Gln Glu Arg Arg Met Ile
            20                  25                  30

Lys Asp Ala Ala Leu His Leu Gln Lys Lys Tyr Gly Thr Tyr Glu Asn
        35                  40                  45

Arg Asp Phe Ile Lys His Val His Gln Leu Ala Ser Tyr Phe Leu Pro
    50                  55                  60

Glu Arg Ile Leu Asn Ile Ala Ala Asp Phe Ala Ser Asp Phe Ser Glu
65                  70                  75                  80

Asn Gln Tyr Gly Ala Leu Val Phe Thr Gly Leu Met Glu Ile Asp Gln
                85                  90                  95

Glu Glu Ile Gly Ser Thr Pro Pro Asn Trp Gln Ser Ala Asp Tyr Ser
            100                 105                 110

Lys Phe Asn Leu Tyr Gly Phe Ala Cys Ala Leu Ile His Gly Ala Leu
        115                 120                 125

Pro Ser Lys Pro Val Gln Tyr Tyr Ser Gln Arg Lys Gly Gly Gly Leu
    130                 135                 140

Ile His Ala Ile Ile Pro Asp Glu Lys Met Lys Glu Thr Gln Thr Gly
145                 150                 155                 160

Ser Gly Ser Ser Thr Asp Leu Tyr Val His Thr Glu Asp Ala Phe Leu
                165                 170                 175

Lys His Gln Ala Asp Phe Leu Ser Phe Met Tyr Val Arg Asn Glu Glu
            180                 185                 190

Gln Val Pro Ser Thr Leu Tyr Ser Ile Arg Ser His Glu Ser Ile Gly
        195                 200                 205

Glu Lys Tyr Arg Thr Leu Phe Glu Pro Ile Tyr Lys Ile Pro Lys Asp
    210                 215                 220
```

```
Ala Asn Leu Glu Thr Gly Glu Asn Glu Glu Thr Leu Asp Ser Val
225                 230                 235                 240

Leu Tyr Gly Asn Thr Asn Leu Pro Phe Met Arg Phe Asp Ala Ala Glu
            245                 250                 255

Gln Leu Phe Asn Ser Ser Ile Arg Gln Ser Glu Glu Ala Gln His Thr
        260                 265                 270

Leu His Glu Phe Trp Glu Ala Arg His Leu Ile Tyr Ser Gly Phe
    275                 280                 285

Thr Pro Gln Ala Gly Asp Val Ile Leu Val Asn Asn His Leu Cys Ala
290                 295                 300

His Gly Arg Ser Ala Phe Arg Ala Gly Val Arg Asn Ile Asp Gly Ile
305                 310                 315                 320

Glu Gln Pro Cys Glu Arg Arg Ile Met Leu Arg Met Met Ser Lys Val
            325                 330                 335

Ser Leu Ile Asp Met Arg Ala His Thr Leu Thr Glu Asp Pro Phe Phe
        340                 345                 350

Val Ile Glu Glu His Leu Gly Lys Asn Phe Gln His Phe
    355                 360                 365
```

<210> SEQ ID NO 9
<211> LENGTH: 1116
<212> TYPE: DNA
<213> ORGANISM: Niastella koreensis NBRC106392
<220> FEATURE:
<221> NAME/KEY: CDS
<222> LOCATION: (1)..(1113)

<400> SEQUENCE: 9

```
atg gaa act atc att gaa tcc aga caa cgc att aac agt ccc ggc gta      48
Met Glu Thr Ile Ile Glu Ser Arg Gln Arg Ile Asn Ser Pro Gly Val
1               5                   10                  15 tta ccg cca cct ttg agt cca ttg atc gtt gac gtt aca ccg aag gag      96
Leu Pro Pro Pro Leu Ser Pro Leu Ile Val Asp Val Thr Pro Lys Glu
            20                  25                  30 cgt gcc tcc att tca aac gtg gcc aat atc tta tta aaa gcc ttt ggc     144
Arg Ala Ser Ile Ser Asn Val Ala Asn Ile Leu Leu Lys Ala Phe Gly
        35                  40                  45 cat tat gaa cat cct gat ttc atc tcc gct ttg cac ctg aat gct ttt     192
His Tyr Glu His Pro Asp Phe Ile Ser Ala Leu His Leu Asn Ala Phe
    50                  55                  60 cag tta tta ccg gaa cgt att gcg ggg ata ctg agc cgt ttt ggt acc     240
Gln Leu Leu Pro Glu Arg Ile Ala Gly Ile Leu Ser Arg Phe Gly Thr
65                  70                  75                  80 gac ttc tcg cgc cac caa tac ggc gcg ttg gtg ttc aga ggc ctt aca     288
Asp Phe Ser Arg His Gln Tyr Gly Ala Leu Val Phe Arg Gly Leu Thr
                85                  90                  95 gaa gta gat cag gag gcg ctt ggc cct acc ccg ccc tcg tgg aaa gaa     336
Glu Val Asp Gln Glu Ala Leu Gly Pro Thr Pro Pro Ser Trp Lys Glu
            100                 105                 110 acc gat tac agc aag ctt gtt aaa tat gga ttt att tgc tcg ctg ctg     384
Thr Asp Tyr Ser Lys Leu Val Lys Tyr Gly Phe Ile Cys Ser Leu Leu
        115                 120                 125 cat ggc gcc att cca tca aaa cca gta caa tat tat gcg cag cga aaa     432
His Gly Ala Ile Pro Ser Lys Pro Val Gln Tyr Tyr Ala Gln Arg Lys
    130                 135                 140 ggc ggt ggt tta ctg cat gcc gtt att ccc gat gaa aaa atg agt cat     480
Gly Gly Gly Leu Leu His Ala Val Ile Pro Asp Glu Lys Met Ser His
145                 150                 155                 160 acg caa acc ggc tcc ggc tcg cgc acc gat ctt ttt gtg cat acc gaa     528
```

```
                    Thr Gln Thr Gly Ser Gly Ser Arg Thr Asp Leu Phe Val His Thr Glu
                            165                 170                 175 gat gcg ttc tta ttt aac cag gcc gat ttt ctc agc ttc ctg ttc ctg          576
Asp Ala Phe Leu Phe Asn Gln Ala Asp Phe Leu Ser Phe Leu Phe Leu
        180                 185                 190 cgg aat gaa gaa cag gtg cca tct acg tta tat tcg atc cgg tcg cat          624
Arg Asn Glu Glu Gln Val Pro Ser Thr Leu Tyr Ser Ile Arg Ser His
            195                 200                 205 ggc gat acc aac gcc atc atg gcg gag ctg ttc aaa ccc att tat aag          672
Gly Asp Thr Asn Ala Ile Met Ala Glu Leu Phe Lys Pro Ile Tyr Lys
        210                 215                 220 tgt ccg aag gat gcg aat tat gcc gac gat gaa aat gcc ggc gag gaa          720
Cys Pro Lys Asp Ala Asn Tyr Ala Asp Asp Glu Asn Ala Gly Glu Glu
225                 230                 235                 240 gtg acc act tct atc tta tac ggt aac cgc gaa cgg ccc ttt atc cgc          768
Val Thr Thr Ser Ile Leu Tyr Gly Asn Arg Glu Arg Pro Phe Ile Arg
                245                 250                 255 ttc gat gcc gcg gaa cag atc tac aac gaa aag gcc gga caa acg ccg          816
Phe Asp Ala Ala Glu Gln Ile Tyr Asn Glu Lys Ala Gly Gln Thr Pro
        260                 265                 270 gaa gcc atg cac aac ctg gtg cgt ttt tgg gac gaa gcc aaa caa ctt          864
Glu Ala Met His Asn Leu Val Arg Phe Trp Asp Glu Ala Lys Gln Leu
            275                 280                 285 atc tac aat gat ttc gtg ccc gat tcg ggc gat ctc att ttt gta aac          912
Ile Tyr Asn Asp Phe Val Pro Asp Ser Gly Asp Leu Ile Phe Val Asn
        290                 295                 300 aac cat ttg tgc gcg cat ggc cgg aat tca ttt gtg gcc ggt tat cgt          960
Asn His Leu Cys Ala His Gly Arg Asn Ser Phe Val Ala Gly Tyr Arg
305                 310                 315                 320 aat gaa aac ggt cag ctg gta aaa tgt gaa cgc cgg ttg atg tta cgc         1008
Asn Glu Asn Gly Gln Leu Val Lys Cys Glu Arg Arg Leu Met Leu Arg
                325                 330                 335 atg atg agc aag acc agc ctc atc aat att cag tcg gtg acc cag tta         1056
Met Met Ser Lys Thr Ser Leu Ile Asn Ile Gln Ser Val Thr Gln Leu
        340                 345                 350 aac gac ccg tat ttc att atg gaa gaa cac tac ggc aaa ttg ttt cat         1104
Asn Asp Pro Tyr Phe Ile Met Glu Glu His Tyr Gly Lys Leu Phe His
            355                 360                 365 tca caa caa taa                                                          1116
Ser Gln Gln
    370

<210> SEQ ID NO 10
<211> LENGTH: 371
<212> TYPE: PRT
<213> ORGANISM: Niastella koreensis NBRC106392

<400> SEQUENCE: 10

Met Glu Thr Ile Ile Glu Ser Arg Gln Arg Ile Asn Ser Pro Gly Val
1               5                   10                  15

Leu Pro Pro Pro Leu Ser Pro Leu Ile Val Asp Val Thr Pro Lys Glu
            20                  25                  30

Arg Ala Ser Ile Ser Asn Val Ala Asn Ile Leu Leu Lys Ala Phe Gly
        35                  40                  45

His Tyr Glu His Pro Asp Phe Ile Ser Ala Leu His Leu Asn Ala Phe
    50                  55                  60

Gln Leu Leu Pro Glu Arg Ile Ala Gly Ile Leu Ser Arg Phe Gly Thr
65                  70                  75                  80

Asp Phe Ser Arg His Gln Tyr Gly Ala Leu Val Phe Arg Gly Leu Thr
```

```
                85                  90                  95
Glu Val Asp Gln Glu Ala Leu Gly Pro Thr Pro Pro Ser Trp Lys Glu
            100                 105                 110

Thr Asp Tyr Ser Lys Leu Val Lys Tyr Gly Phe Ile Cys Ser Leu Leu
            115                 120                 125

His Gly Ala Ile Pro Ser Lys Pro Val Gln Tyr Tyr Ala Gln Arg Lys
    130                 135                 140

Gly Gly Gly Leu Leu His Ala Val Ile Pro Asp Glu Lys Met Ser His
145                 150                 155                 160

Thr Gln Thr Gly Ser Gly Ser Arg Thr Asp Leu Phe Val His Thr Glu
                165                 170                 175

Asp Ala Phe Leu Phe Asn Gln Ala Asp Phe Leu Ser Phe Leu Phe Leu
            180                 185                 190

Arg Asn Glu Glu Gln Val Pro Ser Thr Leu Tyr Ser Ile Arg Ser His
            195                 200                 205

Gly Asp Thr Asn Ala Ile Met Ala Glu Leu Phe Lys Pro Ile Tyr Lys
    210                 215                 220

Cys Pro Lys Asp Ala Asn Tyr Ala Asp Glu Asn Ala Gly Glu Glu
225                 230                 235                 240

Val Thr Thr Ser Ile Leu Tyr Gly Asn Arg Glu Arg Pro Phe Ile Arg
                245                 250                 255

Phe Asp Ala Ala Glu Gln Ile Tyr Asn Glu Lys Ala Gly Gln Thr Pro
            260                 265                 270

Glu Ala Met His Asn Leu Val Arg Phe Trp Asp Glu Ala Lys Gln Leu
            275                 280                 285

Ile Tyr Asn Asp Phe Val Pro Asp Ser Gly Asp Leu Ile Phe Val Asn
    290                 295                 300

Asn His Leu Cys Ala His Gly Arg Asn Ser Phe Val Ala Gly Tyr Arg
305                 310                 315                 320

Asn Glu Asn Gly Gln Leu Val Lys Cys Glu Arg Arg Leu Met Leu Arg
                325                 330                 335

Met Met Ser Lys Thr Ser Leu Ile Asn Ile Gln Ser Val Thr Gln Leu
            340                 345                 350

Asn Asp Pro Tyr Phe Ile Met Glu Glu His Tyr Gly Lys Leu Phe His
            355                 360                 365

Ser Gln Gln
    370

<210> SEQ ID NO 11
<211> LENGTH: 1068
<212> TYPE: DNA
<213> ORGANISM: marine actinobacterium PHSC20C1
<220> FEATURE:
<221> NAME/KEY: CDS
<222> LOCATION: (1)..(1065)

<400> SEQUENCE: 11 atg gaa aca atg tca gca atc gcc cca tct aaa tca cac tta tcg aat     48
Met Glu Thr Met Ser Ala Ile Ala Pro Ser Lys Ser His Leu Ser Asn
1               5                   10                  15 agc tta cgt gtc gca cgc agc aaa gag agc gat att acg gtc cac gaa     96
Ser Leu Arg Val Ala Arg Ser Lys Glu Ser Asp Ile Thr Val His Glu
            20                  25                  30 ctg cag agc agc ctg ttt acg ctg gat tct gct agc gcg gaa gcg atc    144
Leu Gln Ser Ser Leu Phe Thr Leu Asp Ser Ala Ser Ala Glu Ala Ile
        35                  40                  45
```

```
cat acc gcg gct gag cgc att acc gcc cac ccg aac gaa aac ccg gac       192
His Thr Ala Ala Glu Arg Ile Thr Ala His Pro Asn Glu Asn Pro Asp
    50              55              60 gat ttc ggc cgt cag gcg ctg gca gcg gcg ttt agc ttg ccg gaa gag       240
Asp Phe Gly Arg Gln Ala Leu Ala Ala Ala Phe Ser Leu Pro Glu Glu
65              70              75              80 gtg cgt gcg gcg gtc ttg aat ttt gcc gag gtg ggt agc gag agc ggc       288
Val Arg Ala Ala Val Leu Asn Phe Ala Glu Val Gly Ser Glu Ser Gly
                85              90              95 atc atg gtt gtt cgt ggt ctg tac gtg gat gag gac ctg gcc gac acc       336
Ile Met Val Val Arg Gly Leu Tyr Val Asp Glu Asp Leu Ala Asp Thr
            100             105             110 ccg ctg gat aac aag agc ggc ctg ggt gcg cgt acc gtt ttt gcg aaa       384
Pro Leu Asp Asn Lys Ser Gly Leu Gly Ala Arg Thr Val Phe Ala Lys
        115             120             125 gag atg gcc atg ctg gcg cat ctg ctg ggc agc atg gtg gcg tac gag       432
Glu Met Ala Met Leu Ala His Leu Leu Gly Ser Met Val Ala Tyr Glu
130             135             140 gcg gaa ggc aac ggt cat ctg att caa gac atg gtg ccg aat ccg aag       480
Ala Glu Gly Asn Gly His Leu Ile Gln Asp Met Val Pro Asn Pro Lys
145             150             155             160 ctg gcg gtc acg caa caa agc cag ggt agc aag gtt gag ctg gaa gca       528
Leu Ala Val Thr Gln Gln Ser Gln Gly Ser Lys Val Glu Leu Glu Ala
                165             170             175 cat acc gag cag tgc ttc agc gac ttc aaa ccg gat tat gtt att ctg       576
His Thr Glu Gln Cys Phe Ser Asp Phe Lys Pro Asp Tyr Val Ile Leu
            180             185             190 ggt gct ctg cgt ggc gac gaa aac gcc aac acc tat gca ttc tcc ggt       624
Gly Ala Leu Arg Gly Asp Glu Asn Ala Asn Thr Tyr Ala Phe Ser Gly
        195             200             205 cgc aaa ctg gtt cag cac atg tcc gcc gaa gaa gtg gcg aaa ctg cgc       672
Arg Lys Leu Val Gln His Met Ser Ala Glu Glu Val Ala Lys Leu Arg
210             215             220 caa cct ctg tgg gca act acc atc gat gag agc ttt caa ccg tac att       720
Gln Pro Leu Trp Ala Thr Thr Ile Asp Glu Ser Phe Gln Pro Tyr Ile
225             230             235             240 ccg aat ccg gac gac gtt cgc ggt ccg ttc ccg att ctg acg ggc cca       768
Pro Asn Pro Asp Asp Val Arg Gly Pro Phe Pro Ile Leu Thr Gly Pro
                245             250             255 gag gac gat ccg tac atc cgt gta gac cag gag ctg atg cac ggt atc       816
Glu Asp Asp Pro Tyr Ile Arg Val Asp Gln Glu Leu Met His Gly Ile
            260             265             270 acc gcg gac gct caa cgc ctg ctg cgc aag gtt gtg gat acg tat atc       864
Thr Ala Asp Ala Gln Arg Leu Leu Arg Lys Val Val Asp Thr Tyr Ile
        275             280             285 gag cac cgc gac gcg cat gtc ttg cag cct ggt gat ctg ctg atg ctg       912
Glu His Arg Asp Ala His Val Leu Gln Pro Gly Asp Leu Leu Met Leu
290             295             300 gac aat ctg cgt gca atg cac ggt cgt agc atg ttc gct ccg cgt ttt       960
Asp Asn Leu Arg Ala Met His Gly Arg Ser Met Phe Ala Pro Arg Phe
305             310             315             320 gac ggc aag gat cgt ttc att gca cgt ggt ttc gtc gtg cgt gat cgt      1008
Asp Gly Lys Asp Arg Phe Ile Ala Arg Gly Phe Val Val Arg Asp Arg
                325             330             335 cgt aag ttg tgg ccg cag ctg ttg gaa gat cgt cgc acc ctg ggt gca      1056
Arg Lys Leu Trp Pro Gln Leu Leu Glu Asp Arg Arg Thr Leu Gly Ala
            340             345             350 gtc cac tcc taa                                                      1068
Val His Ser
355
```

<210> SEQ ID NO 12
<211> LENGTH: 355
<212> TYPE: PRT
<213> ORGANISM: marine actinobacterium PHSC20C1

<400> SEQUENCE: 12

```
Met Glu Thr Met Ser Ala Ile Ala Pro Ser Lys Ser His Leu Ser Asn
1               5                   10                  15

Ser Leu Arg Val Ala Arg Ser Lys Glu Ser Asp Ile Thr Val His Glu
            20                  25                  30

Leu Gln Ser Ser Leu Phe Thr Leu Asp Ser Ala Ser Glu Ala Ile
        35                  40                  45

His Thr Ala Ala Glu Arg Ile Thr Ala His Pro Asn Glu Asn Pro Asp
    50                  55                  60

Asp Phe Gly Arg Gln Ala Leu Ala Ala Phe Ser Leu Pro Glu Glu
65                  70                  75                  80

Val Arg Ala Ala Val Leu Asn Phe Ala Glu Val Gly Ser Glu Ser Gly
                85                  90                  95

Ile Met Val Val Arg Gly Leu Tyr Val Asp Glu Asp Leu Ala Asp Thr
            100                 105                 110

Pro Leu Asp Asn Lys Ser Gly Leu Gly Ala Arg Thr Val Phe Ala Lys
        115                 120                 125

Glu Met Ala Met Leu Ala His Leu Leu Gly Ser Met Val Ala Tyr Glu
130                 135                 140

Ala Glu Gly Asn Gly His Leu Ile Gln Asp Met Val Pro Asn Pro Lys
145                 150                 155                 160

Leu Ala Val Thr Gln Gln Ser Gln Gly Ser Lys Val Glu Leu Glu Ala
                165                 170                 175

His Thr Glu Gln Cys Phe Ser Asp Phe Lys Pro Asp Tyr Val Ile Leu
            180                 185                 190

Gly Ala Leu Arg Gly Asp Glu Asn Ala Asn Thr Tyr Ala Phe Ser Gly
        195                 200                 205

Arg Lys Leu Val Gln His Met Ser Ala Glu Glu Val Ala Lys Leu Arg
210                 215                 220

Gln Pro Leu Trp Ala Thr Thr Ile Asp Glu Ser Phe Gln Pro Tyr Ile
225                 230                 235                 240

Pro Asn Pro Asp Asp Val Arg Gly Pro Phe Pro Ile Leu Thr Gly Pro
                245                 250                 255

Glu Asp Asp Pro Tyr Ile Arg Val Asp Gln Glu Leu Met His Gly Ile
            260                 265                 270

Thr Ala Asp Ala Gln Arg Leu Leu Arg Lys Val Val Asp Thr Tyr Ile
        275                 280                 285

Glu His Arg Asp Ala His Val Leu Gln Pro Gly Asp Leu Leu Met Leu
290                 295                 300

Asp Asn Leu Arg Ala Met His Gly Arg Ser Met Phe Ala Pro Arg Phe
305                 310                 315                 320

Asp Gly Lys Asp Arg Phe Ile Ala Arg Gly Phe Val Val Arg Asp Arg
                325                 330                 335

Arg Lys Leu Trp Pro Gln Leu Leu Glu Asp Arg Arg Thr Leu Gly Ala
            340                 345                 350

Val His Ser
        355
```

<210> SEQ ID NO 13
<211> LENGTH: 37
<212> TYPE: DNA
<213> ORGANISM: Artificial
<220> FEATURE:
<223> OTHER INFORMATION: PCR primer

<400> SEQUENCE: 13
ttatcatatg aaatcacaat cattaattga agatgag                                37

<210> SEQ ID NO 14
<211> LENGTH: 41
<212> TYPE: DNA
<213> ORGANISM: Artificial
<220> FEATURE:
<223> OTHER INFORMATION: PCR primer

<400> SEQUENCE: 14
tgtaatagct cgagagcctg atcaaaaact tttcctaaat g                           41

<210> SEQ ID NO 15
<211> LENGTH: 31
<212> TYPE: DNA
<213> ORGANISM: Artificial
<220> FEATURE:
<223> OTHER INFORMATION: PCR primer

<400> SEQUENCE: 15
attcacatat gtcctcgctg ttcctcgact c                                      31

<210> SEQ ID NO 16
<211> LENGTH: 30
<212> TYPE: DNA
<213> ORGANISM: Artificial
<220> FEATURE:
<223> OTHER INFORMATION: PCR primer

<400> SEQUENCE: 16
agcttctcga ggctgaagct ggcctgcacg                                        30

<210> SEQ ID NO 17
<211> LENGTH: 32
<212> TYPE: DNA
<213> ORGANISM: Artificial
<220> FEATURE:
<223> OTHER INFORMATION: PCR primer

<400> SEQUENCE: 17
ataatcatat gagacccttta gacgtgacac cc                                    32

<210> SEQ ID NO 18
<211> LENGTH: 38
<212> TYPE: DNA
<213> ORGANISM: Artificial
<220> FEATURE:
<223> OTHER INFORMATION: PCR primer

<400> SEQUENCE: 18
aatagctcga gaaggtttgc caggtgagcg ctatatac                               38

<210> SEQ ID NO 19
<211> LENGTH: 30
<212> TYPE: DNA
<213> ORGANISM: Artificial
<220> FEATURE:
<223> OTHER INFORMATION: PCR primer

```
<400> SEQUENCE: 19
ataatcatat gaattctaca caaattttag                                        30

<210> SEQ ID NO 20
<211> LENGTH: 32
<212> TYPE: DNA
<213> ORGANISM: Artificial
<220> FEATURE:
<223> OTHER INFORMATION: PCR primer

<400> SEQUENCE: 20
aatagctcga gaaaatgttg aaagttttta cc                                     32

<210> SEQ ID NO 21
<211> LENGTH: 29
<212> TYPE: DNA
<213> ORGANISM: Artificial
<220> FEATURE:
<223> OTHER INFORMATION: PCR primer

<400> SEQUENCE: 21
ataatcatat ggaaactatc attgaatcc                                         29

<210> SEQ ID NO 22
<211> LENGTH: 33
<212> TYPE: DNA
<213> ORGANISM: Artificial
<220> FEATURE:
<223> OTHER INFORMATION: PCR primer

<400> SEQUENCE: 22
aatagctcga gttgttgtga atgaaacaat ttg                                    33

<210> SEQ ID NO 23
<211> LENGTH: 1026
<212> TYPE: DNA
<213> ORGANISM: Pseudomonas putida
<220> FEATURE:
<221> NAME/KEY: CDS
<222> LOCATION: (1)..(1023)

<400> SEQUENCE: 23 atg tcc gca cct tcc acc agc acc gtt gtg cgc gtg cct ttt acc gag        48
Met Ser Ala Pro Ser Thr Ser Thr Val Val Arg Val Pro Phe Thr Glu
1               5                   10                  15 ctg caa agc ctg ttg cag gcc att ttc cag cgc cat ggg tgc agc gag        96
Leu Gln Ser Leu Leu Gln Ala Ile Phe Gln Arg His Gly Cys Ser Glu
            20                  25                  30 gcc gtg gcc cgg gtg ctg gcc cac aac tgc gcc agc gcc cag cgt gat       144
Ala Val Ala Arg Val Leu Ala His Asn Cys Ala Ser Ala Gln Arg Asp
        35                  40                  45 ggc gcc cat agc cat ggg gtg ttc cgc atg ccc ggt tat gtc tcg acc       192
Gly Ala His Ser His Gly Val Phe Arg Met Pro Gly Tyr Val Ser Thr
    50                  55                  60 ttg gcc agc ggc tgg gtc gat ggc cag gcc acg cca cag gtc agc gac       240
Leu Ala Ser Gly Trp Val Asp Gly Gln Ala Thr Pro Gln Val Ser Asp
65                  70                  75                  80 gtg gcc gcc ggc tat gtc cgt gtc gat gct gcg ggc ggt ttt gcc cag       288
Val Ala Ala Gly Tyr Val Arg Val Asp Ala Ala Gly Gly Phe Ala Gln
                85                  90                  95 cca gca ctg gcg gcg gcc cgt gag ctg ttg gtg gcg aag gcg cgc agc       336
Pro Ala Leu Ala Ala Ala Arg Glu Leu Leu Val Ala Lys Ala Arg Ser
            100                 105                 110
```

| | | |
|---|---|---|
| gca ggc att gcc gtg ctg gcg atc cac aac tcg cac cac ttc gcc gcg<br>Ala Gly Ile Ala Val Leu Ala Ile His Asn Ser His His Phe Ala Ala<br>115                         120                        125 | 384 |
| cta tgg ccg gat gtc gag ccg ttc gcc gaa gag ggc ctg gta gcc ctc<br>Leu Trp Pro Asp Val Glu Pro Phe Ala Glu Glu Gly Leu Val Ala Leu<br>130                         135                       140 | 432 |
| agc gtg gtc aac agc atg acc tgc gtg gtg ccg cat ggt gca cgc aag<br>Ser Val Val Asn Ser Met Thr Cys Val Val Pro His Gly Ala Arg Lys<br>145                       150                     155                     160 | 480 |
| ccg ctg ttc ggt acc aac ccc atc gct ttt gct gcg cct tgc gcc gag<br>Pro Leu Phe Gly Thr Asn Pro Ile Ala Phe Ala Ala Pro Cys Ala Glu<br>                     165                     170                     175 | 528 |
| cat gac ccg atc gtt ttc gac atg gcc acc agt gcc atg gcc cat ggc<br>His Asp Pro Ile Val Phe Asp Met Ala Thr Ser Ala Met Ala His Gly<br>                180                     185                     190 | 576 |
| gat gtg cag att gcc gcg cgc gcc ggc cag caa ttg ccg gag ggc atg<br>Asp Val Gln Ile Ala Ala Arg Ala Gly Gln Gln Leu Pro Glu Gly Met<br>            195                     200                     205 | 624 |
| ggg gtg gat gcc gat ggc cag ccg acc acc gac ccg aag gcg atc ctg<br>Gly Val Asp Ala Asp Gly Gln Pro Thr Thr Asp Pro Lys Ala Ile Leu<br>210                         215                     220 | 672 |
| gaa ggc ggc gcc ttg ctg cca ttt ggc ggg cac aag ggc tcg gcg ttg<br>Glu Gly Gly Ala Leu Leu Pro Phe Gly Gly His Lys Gly Ser Ala Leu<br>225                       230                     235                    240 | 720 |
| tcg atg atg gtc gag ctg ctg gcg gcg gcg ctg acc ggc ggt cat ttc<br>Ser Met Met Val Glu Leu Leu Ala Ala Ala Leu Thr Gly Gly His Phe<br>                     245                     250                     255 | 768 |
| tcc tgg gag ttc gat tgg tcc ggg cat ccg ggg gcg aaa acg cca tgg<br>Ser Trp Glu Phe Asp Trp Ser Gly His Pro Gly Ala Lys Thr Pro Trp<br>                260                     265                     270 | 816 |
| acc ggg cag ttg atc atc gtc atc aac cca ggc aag gcc gag ggc gag<br>Thr Gly Gln Leu Ile Ile Val Ile Asn Pro Gly Lys Ala Glu Gly Glu<br>            275                     280                     285 | 864 |
| cgc ttt gcc cag cgc agc cgc gag ctg gtg gag cac atg cag gcg gtg<br>Arg Phe Ala Gln Arg Ser Arg Glu Leu Val Glu His Met Gln Ala Val<br>290                         295                     300 | 912 |
| ggg ctg acg cgc atg ccg ggc gag cgg cgc tac cgt gag cgc gag gtg<br>Gly Leu Thr Arg Met Pro Gly Glu Arg Arg Tyr Arg Glu Arg Glu Val<br>305                         310                     315                    320 | 960 |
| gcc gag gag gag ggg gtg gcg gtg acc gag cag gag ttg caa ggc ctg<br>Ala Glu Glu Glu Gly Val Ala Val Thr Glu Gln Glu Leu Gln Gly Leu<br>                     325                     330                     335 | 1008 |
| aaa gag ctg ctt ggc tga<br>Lys Glu Leu Leu Gly<br>            340 | 1026 |

<210> SEQ ID NO 24
<211> LENGTH: 341
<212> TYPE: PRT
<213> ORGANISM: Pseudomonas putida

<400> SEQUENCE: 24

Met Ser Ala Pro Ser Thr Ser Thr Val Val Arg Val Pro Phe Thr Glu
1               5                    10                   15

Leu Gln Ser Leu Leu Gln Ala Ile Phe Gln Arg His Gly Cys Ser Glu
              20                   25                   30

Ala Val Ala Arg Val Leu Ala His Asn Cys Ala Ser Ala Gln Arg Asp
        35                   40                   45

Gly Ala His Ser His Gly Val Phe Arg Met Pro Gly Tyr Val Ser Thr
   50                   55                   60

```
Leu Ala Ser Gly Trp Val Asp Gly Gln Ala Thr Pro Gln Val Ser Asp
 65                  70                  75                  80

Val Ala Ala Gly Tyr Val Arg Val Asp Ala Gly Gly Phe Ala Gln
                 85                  90                  95

Pro Ala Leu Ala Ala Arg Glu Leu Leu Val Ala Lys Ala Arg Ser
            100                 105                 110

Ala Gly Ile Ala Val Leu Ala Ile His Asn Ser His His Phe Ala Ala
            115                 120                 125

Leu Trp Pro Asp Val Glu Pro Phe Ala Glu Glu Gly Leu Val Ala Leu
            130                 135                 140

Ser Val Val Asn Ser Met Thr Cys Val Val Pro His Gly Ala Arg Lys
145                 150                 155                 160

Pro Leu Phe Gly Thr Asn Pro Ile Ala Phe Ala Ala Pro Cys Ala Glu
                165                 170                 175

His Asp Pro Ile Val Phe Asp Met Ala Thr Ser Ala Met Ala His Gly
            180                 185                 190

Asp Val Gln Ile Ala Ala Arg Ala Gly Gln Gln Leu Pro Glu Gly Met
            195                 200                 205

Gly Val Asp Ala Asp Gly Gln Pro Thr Thr Asp Pro Lys Ala Ile Leu
210                 215                 220

Glu Gly Gly Ala Leu Leu Pro Phe Gly His Lys Gly Ser Ala Leu
225                 230                 235                 240

Ser Met Met Val Glu Leu Leu Ala Ala Ala Leu Thr Gly Gly His Phe
                245                 250                 255

Ser Trp Glu Phe Asp Trp Ser Gly His Pro Gly Ala Lys Thr Pro Trp
            260                 265                 270

Thr Gly Gln Leu Ile Ile Val Ile Asn Pro Gly Lys Ala Glu Gly Glu
            275                 280                 285

Arg Phe Ala Gln Arg Ser Arg Glu Leu Val Glu His Met Gln Ala Val
290                 295                 300

Gly Leu Thr Arg Met Pro Gly Glu Arg Arg Tyr Arg Glu Arg Glu Val
305                 310                 315                 320

Ala Glu Glu Glu Gly Val Ala Val Thr Glu Gln Glu Leu Gln Gly Leu
                325                 330                 335

Lys Glu Leu Leu Gly
            340

<210> SEQ ID NO 25
<211> LENGTH: 1488
<212> TYPE: DNA
<213> ORGANISM: Scomber japonicus
<220> FEATURE:
<221> NAME/KEY: CDS
<222> LOCATION: (1)..(1485)

<400> SEQUENCE: 25 atg gag cac ttg gct gat tgc ttg gaa gat aag gat tac gat aca ctt    48
Met Glu His Leu Ala Asp Cys Leu Glu Asp Lys Asp Tyr Asp Thr Leu
 1               5                  10                  15 ttg cag aca ttg gac aac ggt ttg cct cac att aac act tct cat cac    96
Leu Gln Thr Leu Asp Asn Gly Leu Pro His Ile Asn Thr Ser His His
             20                  25                  30 gtt gtc att gtt ggt gcc gga atg gca ggt ttg acc gct gcc aaa ttg   144
Val Val Ile Val Gly Ala Gly Met Ala Gly Leu Thr Ala Ala Lys Leu
         35                  40                  45 ctt caa gat gca gga cac act gtt aca atc ttg gag gct aac gac aga   192
```

```
Leu Gln Asp Ala Gly His Thr Val Thr Ile Leu Glu Ala Asn Asp Arg
    50                  55                  60 gtt ggt gga aga gtc gaa act tac aga aat gaa aag gag ggt tgg tat      240
Val Gly Gly Arg Val Glu Thr Tyr Arg Asn Glu Lys Glu Gly Trp Tyr
 65                  70                  75                  80 gct gaa atg gga gcc atg aga atc cca tct tct cat aga atc gtt cag      288
Ala Glu Met Gly Ala Met Arg Ile Pro Ser Ser His Arg Ile Val Gln
                     85                  90                  95 tgg ttt gtc aag aaa ttg ggt gtt gaa atg aac gag ttt gtc atg aca      336
Trp Phe Val Lys Lys Leu Gly Val Glu Met Asn Glu Phe Val Met Thr
                    100                 105                 110 gat gac aac acc ttc tac ttg gtt aat gga gtc aga gaa aga act tat      384
Asp Asp Asn Thr Phe Tyr Leu Val Asn Gly Val Arg Glu Arg Thr Tyr
                115                 120                 125 gtt gtc caa gag aac cct gat gtt ttg aag tac aat gtc tct gaa tcc      432
Val Val Gln Glu Asn Pro Asp Val Leu Lys Tyr Asn Val Ser Glu Ser
            130                 135                 140 gag aaa ggt att tct gct gat gac ttg ctt gac aga gcc ttg cag aag      480
Glu Lys Gly Ile Ser Ala Asp Asp Leu Leu Asp Arg Ala Leu Gln Lys
145                 150                 155                 160 gtt aaa gaa gag gtc gaa gct aat ggt tgt aag gca gct ttg gag aag      528
Val Lys Glu Glu Val Glu Ala Asn Gly Cys Lys Ala Ala Leu Glu Lys
                    165                 170                 175 tac gat aga tac tct gtt aag gaa tat ttg aaa gaa gag ggt gga ctt      576
Tyr Asp Arg Tyr Ser Val Lys Glu Tyr Leu Lys Glu Glu Gly Gly Leu
                180                 185                 190 tcc cca ggt gct gtt aga atg att gga gat ttg ctt aac gag caa tct      624
Ser Pro Gly Ala Val Arg Met Ile Gly Asp Leu Leu Asn Glu Gln Ser
            195                 200                 205 ttg atg tac act gcc ctt tcc gaa atg atc tat gat cag gca gac gtt      672
Leu Met Tyr Thr Ala Leu Ser Glu Met Ile Tyr Asp Gln Ala Asp Val
210                 215                 220 aat gat tca gtc agt tac cac gag gtt aca ggt gga tcc gat ttg ctt      720
Asn Asp Ser Val Ser Tyr His Glu Val Thr Gly Gly Ser Asp Leu Leu
225                 230                 235                 240 cca gaa gct ttc ttg tca gtt ctt gac gtc cct atc ttg ctt aac tcc      768
Pro Glu Ala Phe Leu Ser Val Leu Asp Val Pro Ile Leu Leu Asn Ser
                    245                 250                 255 aag gtt aag cat atc aga caa tca gat aag ggt gtt atc gtc agt tat      816
Lys Val Lys His Ile Arg Gln Ser Asp Lys Gly Val Ile Val Ser Tyr
                260                 265                 270 cag act gga aat gaa tca agt ttg atg gac ctt tct gct gat att gtt      864
Gln Thr Gly Asn Glu Ser Ser Leu Met Asp Leu Ser Ala Asp Ile Val
            275                 280                 285 ttg gtc act aca acc gcc aaa gcc gca ttg ttt att gat ttc gac cca      912
Leu Val Thr Thr Thr Ala Lys Ala Ala Leu Phe Ile Asp Phe Asp Pro
290                 295                 300 cct ttg tct atc tcc aag atg gag gct ttg aga tct gtt cac tac gat      960
Pro Leu Ser Ile Ser Lys Met Glu Ala Leu Arg Ser Val His Tyr Asp
305                 310                 315                 320 tct tcc act aag atc ttg ctt act ttt aga gac aag ttc tgg gaa gat     1008
Ser Ser Thr Lys Ile Leu Leu Thr Phe Arg Asp Lys Phe Trp Glu Asp
                    325                 330                 335 gac ggt att aga ggt gga aag tca atc aca gat gga cca agt aga tac     1056
Asp Gly Ile Arg Gly Gly Lys Ser Ile Thr Asp Gly Pro Ser Arg Tyr
                340                 345                 350 atc tac tat cct tca cat agt ttt cac acc aac gag act atc ggt gtt     1104
Ile Tyr Tyr Pro Ser His Ser Phe His Thr Asn Glu Thr Ile Gly Val
            355                 360                 365
```

```
ttg ctt gcc tca tat act tgg tct gac gaa tcc ttg ctt ttc ttg gga      1152
Leu Leu Ala Ser Tyr Thr Trp Ser Asp Glu Ser Leu Leu Phe Leu Gly
370                 375                 380 gct tct gat gaa gag ttg aag gag ttg gcc ctt aga gac ttg gca aaa      1200
Ala Ser Asp Glu Glu Leu Lys Glu Leu Ala Leu Arg Asp Leu Ala Lys
385                 390                 395                 400 att cac ggt gaa caa gtt tgg gat aag tgc aca gga gtt atc gtc aag      1248
Ile His Gly Glu Gln Val Trp Asp Lys Cys Thr Gly Val Ile Val Lys
            405                 410                 415 aaa tgg tct gct gac cca tac tcc ttg ggt gca ttt gct ctt ttc acc      1296
Lys Trp Ser Ala Asp Pro Tyr Ser Leu Gly Ala Phe Ala Leu Phe Thr
420                 425                 430 cct tac caa cat ttg gaa tat gca cag gag ttg ttt tct tct gaa ggt      1344
Pro Tyr Gln His Leu Glu Tyr Ala Gln Glu Leu Phe Ser Ser Glu Gly
435                 440                 445 aga gtt cat ttt gct gga gag cac acc gca ttc cct cat gct tgg att      1392
Arg Val His Phe Ala Gly Glu His Thr Ala Phe Pro His Ala Trp Ile
    450                 455                 460 gaa act tca atg aaa agt gct atc aga gct gcc aca aac att aac aaa      1440
Glu Thr Ser Met Lys Ser Ala Ile Arg Ala Ala Thr Asn Ile Asn Lys
465                 470                 475                 480 gtc gct aac gaa gaa tcc acc att gaa cac aca aaa gat gag ttg taa      1488
Val Ala Asn Glu Glu Ser Thr Ile Glu His Thr Lys Asp Glu Leu
                485                 490                 495

<210> SEQ ID NO 26
<211> LENGTH: 495
<212> TYPE: PRT
<213> ORGANISM: Scomber japonicus

<400> SEQUENCE: 26

Met Glu His Leu Ala Asp Cys Leu Glu Asp Lys Asp Tyr Asp Thr Leu
1               5                   10                  15

Leu Gln Thr Leu Asp Asn Gly Leu Pro His Ile Asn Thr Ser His His
            20                  25                  30

Val Val Ile Val Gly Ala Gly Met Ala Gly Leu Thr Ala Ala Lys Leu
        35                  40                  45

Leu Gln Asp Ala Gly His Thr Val Thr Ile Leu Glu Ala Asn Asp Arg
    50                  55                  60

Val Gly Gly Arg Val Glu Thr Tyr Arg Asn Glu Lys Glu Gly Trp Tyr
65                  70                  75                  80

Ala Glu Met Gly Ala Met Arg Ile Pro Ser Ser His Arg Ile Val Gln
                85                  90                  95

Trp Phe Val Lys Lys Leu Gly Val Glu Met Asn Glu Phe Val Met Thr
            100                 105                 110

Asp Asp Asn Thr Phe Tyr Leu Val Asn Gly Val Arg Glu Arg Thr Tyr
        115                 120                 125

Val Val Gln Glu Asn Pro Asp Val Leu Lys Tyr Asn Val Ser Glu Ser
    130                 135                 140

Glu Lys Gly Ile Ser Ala Asp Asp Leu Leu Asp Arg Ala Leu Gln Lys
145                 150                 155                 160

Val Lys Glu Glu Val Glu Ala Asn Gly Cys Lys Ala Ala Leu Glu Lys
                165                 170                 175

Tyr Asp Arg Tyr Ser Val Lys Glu Tyr Leu Lys Glu Glu Gly Gly Leu
            180                 185                 190

Ser Pro Gly Ala Val Arg Met Ile Gly Asp Leu Leu Asn Glu Gln Ser
        195                 200                 205
```

```
Leu Met Tyr Thr Ala Leu Ser Glu Met Ile Tyr Asp Gln Ala Asp Val
    210                 215                 220

Asn Asp Ser Val Ser Tyr His Glu Val Thr Gly Gly Ser Asp Leu Leu
225                 230                 235                 240

Pro Glu Ala Phe Leu Ser Val Leu Asp Val Pro Ile Leu Leu Asn Ser
                245                 250                 255

Lys Val Lys His Ile Arg Gln Ser Asp Lys Gly Val Ile Val Ser Tyr
            260                 265                 270

Gln Thr Gly Asn Glu Ser Ser Leu Met Asp Leu Ser Ala Asp Ile Val
        275                 280                 285

Leu Val Thr Thr Thr Ala Lys Ala Ala Leu Phe Ile Asp Phe Asp Pro
    290                 295                 300

Pro Leu Ser Ile Ser Lys Met Glu Ala Leu Arg Ser Val His Tyr Asp
305                 310                 315                 320

Ser Ser Thr Lys Ile Leu Leu Thr Phe Arg Asp Lys Phe Trp Glu Asp
                325                 330                 335

Asp Gly Ile Arg Gly Gly Lys Ser Ile Thr Asp Gly Pro Ser Arg Tyr
            340                 345                 350

Ile Tyr Tyr Pro Ser His Ser Phe His Thr Asn Glu Thr Ile Gly Val
        355                 360                 365

Leu Leu Ala Ser Tyr Thr Trp Ser Asp Glu Ser Leu Leu Phe Leu Gly
    370                 375                 380

Ala Ser Asp Glu Glu Leu Lys Glu Leu Ala Leu Arg Asp Leu Ala Lys
385                 390                 395                 400

Ile His Gly Glu Gln Val Trp Asp Lys Cys Thr Gly Val Ile Val Lys
                405                 410                 415

Lys Trp Ser Ala Asp Pro Tyr Ser Leu Gly Ala Phe Ala Leu Phe Thr
            420                 425                 430

Pro Tyr Gln His Leu Glu Tyr Ala Gln Glu Leu Phe Ser Ser Glu Gly
        435                 440                 445

Arg Val His Phe Ala Gly Glu His Thr Ala Phe Pro His Ala Trp Ile
    450                 455                 460

Glu Thr Ser Met Lys Ser Ala Ile Arg Ala Ala Thr Asn Ile Asn Lys
465                 470                 475                 480

Val Ala Asn Glu Glu Ser Thr Ile Glu His Thr Lys Asp Glu Leu
                485                 490                 495

<210> SEQ ID NO 27
<211> LENGTH: 786
<212> TYPE: DNA
<213> ORGANISM: Bacillus subtilis
<220> FEATURE:
<221> NAME/KEY: CDS
<222> LOCATION: (1)..(783)

<400> SEQUENCE: 27 atg tat ccg gat tta aaa gga aaa gtc gtc gct att aca gga gct gct       48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca       96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta      144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga      192
Lys Glu Glu Val Ile Lys Ala Gly Gly Glu Ala Val Val Val Gln Gly
```

```
                    50                      55                      60
gat  gtc  acg  aaa  gag  gaa  gat  gta  aaa  aat  atc  gtg  caa  acg  gca  att        240
Asp  Val  Thr  Lys  Glu  Glu  Asp  Val  Lys  Asn  Ile  Val  Gln  Thr  Ala  Ile
65                       70                       75                       80 aag  gag  ttc  ggc  aca  ctc  gat  att  atg  att  aat  aat  gcc  ggt  ctt  gca        288
Lys  Glu  Phe  Gly  Thr  Leu  Asp  Ile  Met  Ile  Asn  Asn  Ala  Gly  Leu  Ala
                              85                       90                       95 aat  cct  gtg  cca  tct  cac  gaa  atg  ccg  ctc  aag  gat  tgg  gat  aaa  gtc        336
Asn  Pro  Val  Pro  Ser  His  Glu  Met  Pro  Leu  Lys  Asp  Trp  Asp  Lys  Val
                    100                      105                      110 atc  ggc  acg  aac  tta  acg  ggt  gcc  ttt  tta  gga  agc  cgt  gaa  gcg  att        384
Ile  Gly  Thr  Asn  Leu  Thr  Gly  Ala  Phe  Leu  Gly  Ser  Arg  Glu  Ala  Ile
          115                      120                      125 aaa  tat  ttc  gta  gaa  aac  gat  atc  aag  gga  aat  gtc  att  aac  atg  tcc        432
Lys  Tyr  Phe  Val  Glu  Asn  Asp  Ile  Lys  Gly  Asn  Val  Ile  Asn  Met  Ser
130                      135                      140 agt  gtg  cac  gaa  gtg  att  cct  tgg  ccg  tta  ttt  gtc  cac  tat  gcg  gca        480
Ser  Val  His  Glu  Val  Ile  Pro  Trp  Pro  Leu  Phe  Val  His  Tyr  Ala  Ala
145                      150                      155                      160 agt  aaa  ggc  ggg  ata  aag  ctg  atg  aca  gaa  aca  tta  gcg  ttg  gaa  tac        528
Ser  Lys  Gly  Gly  Ile  Lys  Leu  Met  Thr  Glu  Thr  Leu  Ala  Leu  Glu  Tyr
                    165                      170                      175 gcg  ccg  aag  ggc  att  cgc  gtc  aat  aat  att  ggg  cca  ggt  gcg  atc  aac        576
Ala  Pro  Lys  Gly  Ile  Arg  Val  Asn  Asn  Ile  Gly  Pro  Gly  Ala  Ile  Asn
                         180                      185                      190 acg  cca  atc  aat  gct  gaa  aaa  ttc  gct  gac  cct  aaa  cag  aaa  gct  gat        624
Thr  Pro  Ile  Asn  Ala  Glu  Lys  Phe  Ala  Asp  Pro  Lys  Gln  Lys  Ala  Asp
               195                      200                      205 gta  gaa  agc  atg  att  cca  atg  gga  tat  atc  ggc  gaa  ccg  gag  gag  atc        672
Val  Glu  Ser  Met  Ile  Pro  Met  Gly  Tyr  Ile  Gly  Glu  Pro  Glu  Glu  Ile
     210                      215                      220 gcc  gca  gta  gca  gcc  tgg  ctt  gct  tcg  aag  gaa  gcc  agc  tac  gtc  aca        720
Ala  Ala  Val  Ala  Ala  Trp  Leu  Ala  Ser  Lys  Glu  Ala  Ser  Tyr  Val  Thr
225                      230                      235                      240 ggc  atc  acg  tta  ttc  gcg  gac  ggc  ggt  atg  aca  caa  tat  cct  tca  ttc        768
Gly  Ile  Thr  Leu  Phe  Ala  Asp  Gly  Gly  Met  Thr  Gln  Tyr  Pro  Ser  Phe
                    245                      250                      255 cag  gca  ggc  cgc  ggt  taa                                                          786
Gln  Ala  Gly  Arg  Gly
               260
```

<210> SEQ ID NO 28
<211> LENGTH: 261
<212> TYPE: PRT
<213> ORGANISM: Bacillus subtilis

<400> SEQUENCE: 28

```
Met  Tyr  Pro  Asp  Leu  Lys  Gly  Lys  Val  Val  Ala  Ile  Thr  Gly  Ala  Ala
1                   5                       10                      15

Ser  Gly  Leu  Gly  Lys  Ala  Met  Ala  Ile  Arg  Phe  Gly  Lys  Glu  Gln  Ala
               20                      25                      30

Lys  Val  Val  Ile  Asn  Tyr  Tyr  Ser  Asn  Lys  Gln  Asp  Pro  Asn  Glu  Val
           35                      40                      45

Lys  Glu  Glu  Val  Ile  Lys  Ala  Gly  Gly  Glu  Ala  Val  Val  Val  Gln  Gly
     50                      55                      60

Asp  Val  Thr  Lys  Glu  Glu  Asp  Val  Lys  Asn  Ile  Val  Gln  Thr  Ala  Ile
65                       70                      75                       80

Lys  Glu  Phe  Gly  Thr  Leu  Asp  Ile  Met  Ile  Asn  Asn  Ala  Gly  Leu  Ala
               85                      90                      95
```

```
Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 29
<211> LENGTH: 1230
<212> TYPE: DNA
<213> ORGANISM: Pseudomonas putida
<220> FEATURE:
<221> NAME/KEY: CDS
<222> LOCATION: (1)..(1227)

<400> SEQUENCE: 29
```

| | | | | | | | | | | | | | | | | |
|---|---|---|---|---|---|---|---|---|---|---|---|---|---|---|---|---|
| atg | ccc | ttt | cgc | cgt | acc | ctt | ctg | gct | gca | tcc | ctg | gca | ctt | ctg | atc | 48 |
| Met | Pro | Phe | Arg | Arg | Thr | Leu | Leu | Ala | Ala | Ser | Leu | Ala | Leu | Leu | Ile | |
| 1 | | | | 5 | | | | | 10 | | | | | 15 | | |
| acc | gga | cag | gcc | ccc | ctg | tat | gcg | gca | cca | ccg | ttg | tcg | atg | gac | aac | 96 |
| Thr | Gly | Gln | Ala | Pro | Leu | Tyr | Ala | Ala | Pro | Pro | Leu | Ser | Met | Asp | Asn | |
| | | | 20 | | | | | 25 | | | | | 30 | | | |
| ggc | acc | aac | acc | ctg | acc | gtg | caa | aac | agc | aat | gcc | tgg | gtc | gaa | gtc | 144 |
| Gly | Thr | Asn | Thr | Leu | Thr | Val | Gln | Asn | Ser | Asn | Ala | Trp | Val | Glu | Val | |
| | | 35 | | | | | 40 | | | | | 45 | | | | |
| agc | gcc | agc | gcc | ctg | cag | cac | aac | atc | cgc | acg | ctg | cag | gcc | gag | ctg | 192 |
| Ser | Ala | Ser | Ala | Leu | Gln | His | Asn | Ile | Arg | Thr | Leu | Gln | Ala | Glu | Leu | |
| | 50 | | | | | 55 | | | | | 60 | | | | | |
| gcc | ggc | aag | tcc | aag | ctg | tgc | gcc | gtg | ctc | aag | gcc | gat | gcc | tat | ggc | 240 |
| Ala | Gly | Lys | Ser | Lys | Leu | Cys | Ala | Val | Leu | Lys | Ala | Asp | Ala | Tyr | Gly | |
| 65 | | | | | 70 | | | | | 75 | | | | | 80 | |
| cac | ggt | atc | ggc | ctg | gta | atg | cca | tcg | atc | atc | gcc | caa | ggc | gtg | ccc | 288 |
| His | Gly | Ile | Gly | Leu | Val | Met | Pro | Ser | Ile | Ile | Ala | Gln | Gly | Val | Pro | |
| | | | | 85 | | | | | 90 | | | | | 95 | | |
| tgc | gtg | gcg | gtg | gcc | agc | aac | gag | gag | gcc | cgc | gtg | gtc | cgc | gcc | agt | 336 |
| Cys | Val | Ala | Val | Ala | Ser | Asn | Glu | Glu | Ala | Arg | Val | Val | Arg | Ala | Ser | |
| | | | 100 | | | | | 105 | | | | | 110 | | | |
| ggc | ttc | acc | ggg | caa | ctg | gtg | cgg | gta | cgc | ctg | gcc | agc | ctc | agc | gag | 384 |
| Gly | Phe | Thr | Gly | Gln | Leu | Val | Arg | Val | Arg | Leu | Ala | Ser | Leu | Ser | Glu | |
| | | 115 | | | | | 120 | | | | | 125 | | | | |
| ctg | gaa | gat | ggc | ttg | cag | tac | gac | atg | gaa | gag | ctg | gtg | ggc | agc | gcg | 432 |
| Leu | Glu | Asp | Gly | Leu | Gln | Tyr | Asp | Met | Glu | Glu | Leu | Val | Gly | Ser | Ala | |

```
                130                 135                 140
gaa ttt gcc cgc cag gcc gat gcc atc gcc gcg cgc cat ggc aag acc    480
Glu Phe Ala Arg Gln Ala Asp Ala Ile Ala Ala Arg His Gly Lys Thr
145                 150                 155                 160 ttg cgc att cac atg gcg ctc aac tcc agc ggc atg agc cgc aac ggg    528
Leu Arg Ile His Met Ala Leu Asn Ser Ser Gly Met Ser Arg Asn Gly
                165                 170                 175 gtg gag atg gcc acc tgg tcc ggc cgt ggc gaa gcg ctg cag atc acc    576
Val Glu Met Ala Thr Trp Ser Gly Arg Gly Glu Ala Leu Gln Ile Thr
            180                 185                 190 gac cag aag cac ctc aag ctg gtc gcg ctg atg acc cac ttc gcc gtg    624
Asp Gln Lys His Leu Lys Leu Val Ala Leu Met Thr His Phe Ala Val
        195                 200                 205 gaa gac aag gac gat gta cgc aag ggc ctg gcg gca ttc aac gag cag    672
Glu Asp Lys Asp Asp Val Arg Lys Gly Leu Ala Ala Phe Asn Glu Gln
    210                 215                 220 acc gac tgg ttg atc aag cac gcc agg ctg gac cgc agc aag ctc acc    720
Thr Asp Trp Leu Ile Lys His Ala Arg Leu Asp Arg Ser Lys Leu Thr
225                 230                 235                 240 ctg cac gcc gcc aac tcg ttc gct acg ctg gaa gtg ccg gaa gcg cgc    768
Leu His Ala Ala Asn Ser Phe Ala Thr Leu Glu Val Pro Glu Ala Arg
                245                 250                 255 ctg gac atg gta cga acg ggt ggc gcg ctg ttc ggc gac acc gtg ccg    816
Leu Asp Met Val Arg Thr Gly Gly Ala Leu Phe Gly Asp Thr Val Pro
            260                 265                 270 gcg cgc acc gag tac aaa cgt gcg atg cag ttc aaa tcg cac gtg gcg    864
Ala Arg Thr Glu Tyr Lys Arg Ala Met Gln Phe Lys Ser His Val Ala
        275                 280                 285 gcg gtg cac agc tat ccg gcc ggc aac acc gtg ggc tat gac cgc acc    912
Ala Val His Ser Tyr Pro Ala Gly Asn Thr Val Gly Tyr Asp Arg Thr
    290                 295                 300 ttc acc ctg gcc cgt gat tcg cgg ctg gcc aac att acg gtc ggg tac    960
Phe Thr Leu Ala Arg Asp Ser Arg Leu Ala Asn Ile Thr Val Gly Tyr
305                 310                 315                 320 tcc gat ggc tac cgc cgg gta ttc acc aac aag ggc cat gtg ctg atc    1008
Ser Asp Gly Tyr Arg Arg Val Phe Thr Asn Lys Gly His Val Leu Ile
                325                 330                 335 aac ggc cac cgt gtg ccg gtc gtg ggc aag gtg tcg atg aac acg ctg    1056
Asn Gly His Arg Val Pro Val Val Gly Lys Val Ser Met Asn Thr Leu
            340                 345                 350 atg gtc gat gtc acc gac ttc cct gat gtg aag ggg ggt aac gaa gtg    1104
Met Val Asp Val Thr Asp Phe Pro Asp Val Lys Gly Gly Asn Glu Val
        355                 360                 365 gtg ctg ttc ggc aag cag gcc ggg ggc gaa atc acc cag gcc gag atg    1152
Val Leu Phe Gly Lys Gln Ala Gly Gly Glu Ile Thr Gln Ala Glu Met
    370                 375                 380 gaa gaa atc aac ggc gcg ttg ctc gcc gat ttg tac acc gta tgg ggc    1200
Glu Glu Ile Asn Gly Ala Leu Leu Ala Asp Leu Tyr Thr Val Trp Gly
385                 390                 395                 400 aat tcc aac ccg aag ata ctc gtc gac tga                            1230
Asn Ser Asn Pro Lys Ile Leu Val Asp
                405

<210> SEQ ID NO 30
<211> LENGTH: 409
<212> TYPE: PRT
<213> ORGANISM: Pseudomonas putida

<400> SEQUENCE: 30

Met Pro Phe Arg Arg Thr Leu Leu Ala Ala Ser Leu Ala Leu Leu Ile
```

```
  1               5                   10                  15
Thr Gly Gln Ala Pro Leu Tyr Ala Ala Pro Leu Ser Met Asp Asn
             20                  25                  30
Gly Thr Asn Thr Leu Thr Val Gln Asn Ser Asn Ala Trp Val Glu Val
             35                  40                  45
Ser Ala Ser Ala Leu Gln His Asn Ile Arg Thr Leu Gln Ala Glu Leu
 50                  55                  60
Ala Gly Lys Ser Lys Leu Cys Ala Val Leu Lys Ala Asp Ala Tyr Gly
 65                  70                  75                  80
His Gly Ile Gly Leu Val Met Pro Ser Ile Ile Ala Gln Gly Val Pro
             85                  90                  95
Cys Val Ala Val Ala Ser Asn Glu Glu Ala Arg Val Val Arg Ala Ser
                 100                 105                 110
Gly Phe Thr Gly Gln Leu Val Arg Val Arg Leu Ala Ser Leu Ser Glu
             115                 120                 125
Leu Glu Asp Gly Leu Gln Tyr Asp Met Glu Glu Leu Val Gly Ser Ala
 130                 135                 140
Glu Phe Ala Arg Gln Ala Asp Ala Ile Ala Ala Arg His Gly Lys Thr
 145                 150                 155                 160
Leu Arg Ile His Met Ala Leu Asn Ser Ser Gly Met Ser Arg Asn Gly
                 165                 170                 175
Val Glu Met Ala Thr Trp Ser Gly Arg Gly Glu Ala Leu Gln Ile Thr
             180                 185                 190
Asp Gln Lys His Leu Lys Leu Val Ala Leu Met Thr His Phe Ala Val
                 195                 200                 205
Glu Asp Lys Asp Asp Val Arg Lys Gly Leu Ala Ala Phe Asn Glu Gln
 210                 215                 220
Thr Asp Trp Leu Ile Lys His Ala Arg Leu Asp Arg Ser Lys Leu Thr
 225                 230                 235                 240
Leu His Ala Ala Asn Ser Phe Ala Thr Leu Glu Val Pro Glu Ala Arg
                 245                 250                 255
Leu Asp Met Val Arg Thr Gly Gly Ala Leu Phe Gly Asp Thr Val Pro
             260                 265                 270
Ala Arg Thr Glu Tyr Lys Arg Ala Met Gln Phe Lys Ser His Val Ala
             275                 280                 285
Ala Val His Ser Tyr Pro Ala Gly Asn Thr Val Gly Tyr Asp Arg Thr
             290                 295                 300
Phe Thr Leu Ala Arg Asp Ser Arg Leu Ala Asn Ile Thr Val Gly Tyr
 305                 310                 315                 320
Ser Asp Gly Tyr Arg Arg Val Phe Thr Asn Lys Gly His Val Leu Ile
                 325                 330                 335
Asn Gly His Arg Val Pro Val Val Gly Lys Val Ser Met Asn Thr Leu
                 340                 345                 350
Met Val Asp Val Thr Asp Phe Pro Asp Val Lys Gly Gly Asn Glu Val
                 355                 360                 365
Val Leu Phe Gly Lys Gln Ala Gly Gly Glu Ile Thr Gln Ala Glu Met
             370                 375                 380
Glu Glu Ile Asn Gly Ala Leu Leu Ala Asp Leu Tyr Thr Val Trp Gly
 385                 390                 395                 400
Asn Ser Asn Pro Lys Ile Leu Val Asp
                 405

<210> SEQ ID NO 31
```

```
<211> LENGTH: 36
<212> TYPE: DNA
<213> ORGANISM: Artificial sequence
<220> FEATURE:
<223> OTHER INFORMATION: PCR primer

<400> SEQUENCE: 31
gcgaattcat gtccgcacct tccaccagca ccgttg                    36

<210> SEQ ID NO 32
<211> LENGTH: 36
<212> TYPE: DNA
<213> ORGANISM: Artificial sequence
<220> FEATURE:
<223> OTHER INFORMATION: PCR primer

<400> SEQUENCE: 32
gctctagatc agccaagcag ctctttcagg ccttgc                    36

<210> SEQ ID NO 33
<211> LENGTH: 41
<212> TYPE: DNA
<213> ORGANISM: Artificial sequence
<220> FEATURE:
<223> OTHER INFORMATION: PCR primer

<400> SEQUENCE: 33
gcgaattcat ggagcacttg gctgattgct tggaagataa g              41

<210> SEQ ID NO 34
<211> LENGTH: 39
<212> TYPE: DNA
<213> ORGANISM: Artificial sequence
<220> FEATURE:
<223> OTHER INFORMATION: PCR primer

<400> SEQUENCE: 34
gctctagatt acaactcatc ttttgtgtgt tcaatggtg                 39

<210> SEQ ID NO 35
<211> LENGTH: 37
<212> TYPE: DNA
<213> ORGANISM: Artificial sequence
<220> FEATURE:
<223> OTHER INFORMATION: PCR primer

<400> SEQUENCE: 35
ggggaattca tgtatccgga tttaaaagga aaagtcg                   37

<210> SEQ ID NO 36
<211> LENGTH: 28
<212> TYPE: DNA
<213> ORGANISM: Artificial sequence
<220> FEATURE:
<223> OTHER INFORMATION: PCR primer

<400> SEQUENCE: 36
ggggtctaga ttaaccgcgg cctgcctg                             28

<210> SEQ ID NO 37
<211> LENGTH: 36
<212> TYPE: DNA
<213> ORGANISM: Artificial sequence
<220> FEATURE:
<223> OTHER INFORMATION: PCR primer

<400> SEQUENCE: 37
```

```
gcgaattcat gcccttctgc cgtaccttc tggctg                                36
```

<210> SEQ ID NO 38
<211> LENGTH: 39
<212> TYPE: DNA
<213> ORGANISM: Artificial sequence
<220> FEATURE:
<223> OTHER INFORMATION: PCR primer

<400> SEQUENCE: 38

```
gctctagatc agtcgacgag tatcttcggg ttggaattg                            39
```